(12) United States Patent
Devane

(10) Patent No.: US 9,040,591 B2
(45) Date of Patent: May 26, 2015

(54) METHODS AND COMPOSITIONS COMPRISING AT LEAST ONE α3 βA4 NACHR ANTAGONIST OR PHARMACEUTICALLY ACCEPTABLE SALT THEREOF

(75) Inventor: John Devane, Roscommon (IE)

(73) Assignee: AGI Therapeutics Public Limited Company, Dublin (IE)

( * ) Notice: Subject to any disclaimer, the term of this patent is extended or adjusted under 35 U.S.C. 154(b) by 0 days.

(21) Appl. No.: 13/553,453

(22) Filed: Jul. 19, 2012

(65) Prior Publication Data

US 2013/0030057 A1    Jan. 31, 2013

Related U.S. Application Data

(63) Continuation of application No. 12/724,652, filed on Mar. 16, 2010, now abandoned, which is a continuation of application No. 11/698,131, filed on Jan. 26, 2007, now abandoned, which is a (Continued)

(51) Int. Cl.
*A61K 31/13*    (2006.01)
*A61P 13/00*    (2006.01)

(Continued)

(52) U.S. Cl.
CPC ............ *A61K 45/06* (2013.01); *A61K 31/13* (2013.01); *A61K 31/135* (2013.01); *A61K 31/14* (2013.01); *A61K 31/225* (2013.01); *A61K 31/34* (2013.01); *A61K 31/40* (2013.01); *A61K 31/415* (2013.01); *A61K 31/44* (2013.01); *A61K 31/445* (2013.01);

(Continued)

(58) Field of Classification Search
CPC . A61K 2300/00; A61K 31/13; A61K 31/135; A61K 31/14; A61K 31/225; A61K 31/34; A61K 31/40; A61K 31/415; A61K 31/44; A61K 31/445; A61K 31/47; A61K 31/4965; A61K 31/497; A61K 31/56; A61K 31/72
USPC ......................................................... 514/661
See application file for complete search history.

(56) References Cited

U.S. PATENT DOCUMENTS 6,034,079 A    3/2000    Sanberg et al.
6,121,289 A    9/2000    Houdi (Continued)

FOREIGN PATENT DOCUMENTS

WO    WO 00/33812    6/2000
WO    WO 00/35279    6/2000

(Continued)

OTHER PUBLICATIONS

Mangel, "Production of Colonic Contractility to Cholecystokinin and Other Peptides," *European Journal of Pharmacology*, 100 (1984) pp. 285-290.

(Continued)

*Primary Examiner* — Savitha Rao
(74) *Attorney, Agent, or Firm* — Finnegan, Henderson, Farabow, Garrett & Dunner LLP

(57) ABSTRACT

The present invention is directed to methods and formulations for treating, modifying, and/or managing gastrointestinal secretion, and intestinal conditions that cause the same. Methods of using at least one α3 β4 nAChR antagonist and formulations comprising at least one α3 β4 nAChR antagonist, or pharmaceutically acceptable salt thereof, are included.

12 Claims, 2 Drawing Sheets

Related U.S. Application Data continuation-in-part of application No. 10/798,421, filed on Mar. 12, 2004, now abandoned.

(60) Provisional application No. 60/454,527, filed on Mar. 14, 2003.

(51) Int. Cl.

| | |
|---|---|
| *A61P 21/02* | (2006.01) |
| *A61P 9/00* | (2006.01) |
| *A61K 45/06* | (2006.01) |
| *A61K 31/135* | (2006.01) |
| *A61K 31/14* | (2006.01) |
| *A61K 31/225* | (2006.01) |
| *A61K 31/34* | (2006.01) |
| *A61K 31/40* | (2006.01) |
| *A61K 31/415* | (2006.01) |
| *A61K 31/44* | (2006.01) |
| *A61K 31/445* | (2006.01) |
| *A61K 31/47* | (2006.01) |
| *A61K 31/4965* | (2006.01) |
| *A61K 31/497* | (2006.01) |
| *A61K 31/56* | (2006.01) |
| *A61K 31/727* | (2006.01) |
| *A61K 33/24* | (2006.01) |
| *A61K 35/60* | (2006.01) |
| *A61K 38/13* | (2006.01) |

(52) U.S. Cl.
CPC .............. *A61K 31/47* (2013.01); *A61K 31/4965* (2013.01); *A61K 31/497* (2013.01); *A61K 31/56* (2013.01); *A61K 31/727* (2013.01); *A61K 33/24* (2013.01); *A61K 35/60* (2013.01); *A61K 38/13* (2013.01)

(56) References Cited

U.S. PATENT DOCUMENTS

| | | |
|---|---|---|
| 2001/0014678 A1 | 8/2001 | Cary |
| 2002/0004065 A1 | 1/2002 | Kanios |
| 2002/0016370 A1 | 2/2002 | Shytle et al. |
| 2002/0016371 A1 | 2/2002 | Shytle et al. |
| 2002/0103109 A1 | 8/2002 | Glick et al. |
| 2003/0199439 A1 | 10/2003 | Simon |
| 2004/0209961 A1 | 10/2004 | Devane |

FOREIGN PATENT DOCUMENTS

| | | |
|---|---|---|
| WO | WO 00/35280 | 6/2000 |
| WO | WO 03/090731 | 11/2003 |

OTHER PUBLICATIONS

Braida, et al., "Excitatory and Inhibitory Effects of Second-Generation Cholinesterase Inhibitors on Rat Gastrointestinal Transit," *Pharmacological Research*, vol. 41, No. 6, (2000) pp. 671-677.

Kachur, et al., "Pharmacological effects of 1,2,3,5,6,10b-hexahydropyrido[2,3g]indolozine, a bridged-nicotine analog," *Life Scii.*, 38(4), pp. 323-330 (1986).

Nordberg, et al., "Uptake and regional distribution of (+)-(R)- and (−)(S)-N-[methyl-$^{11}$C]-nicotine in the brains of Rhesus monkey. An attempt to study nicotinic receptors in vivo," *J. Neural Transm. Park Dis. Dement. Sect.*, 1(3): pp. 195-205 (1989).

Papke, et al., "Analysis of mecamylamine stereoisomers on human nicotinic receptor subtypes," *J. Pharmacol. Exp. Ther.*, 297(2), pp. 646-656 (2001).

Sloan, et al., "Nature of nicotine binding to rat brain $P_2$ fraction," *Pharmacol. Biochem Behav.*, 20(6), pp. 899-909 (1984).

Sloan, et al., "The comparative binding characteristics of nicotinic ligands and their pharmacology," *Pharmacol. Biochem. Behav.*, 30(1), pp. 255-267 (1988).

Targacept press release entitled "Targacept and Dr. Falk Pharma Successfully Complete Phase I Studies of First in Class Drug for Ulcerative Colitisu," Winston-Salem, NC, Oct. 1, 2002.

Young, et al., "Mecamylamine: new therapeutic uses and toxicity/risk profile," *Clincal Therapeutics* 23(4), pp. 532-565 (2001).

Zevin, et al., "Nicotine-mecamylamine interactions," *Clin. Pharmacol. Ther.*, 68(1), pp. 58-66 (2000).

Garg, K. N., "Effects of mecamylamine and pemppidine on the motility of small intestine in different species of animals," *Indian Journal of Medical Research*, vol. 54, No. 11, (Nov. 1, 1966), pp. 1057-1059, ISSN: 0971-5916, XP009105700.

Summers, R. W., et al., "Effects of Drugs, Ileal Obstruction, and Irradiation on Rat Gastrointestinal Propulsion," *Gastroenterology*, Elsevier, Philadelphia, PA, vol. 59, No. 5, (Jan. 1, 1970), pp. 731-739, ISSN: 0016-5085, XP009033303.

METHODS AND COMPOSITIONS COMPRISING AT LEAST ONE α3 βA4 NACHR ANTAGONIST OR PHARMACEUTICALLY ACCEPTABLE SALT THEREOF

This application is a continuation of U.S. application Ser. No. 12/724,652, filed Mar. 16, 2010 now abandoned, which is a continuation of U.S. Non-provisional application Ser. No. 11/698,131, filed Jan. 26, 2007 now abandoned, which is a continuation-in-part and claims the benefit of U.S. Non-provisional application Ser. No. 10/798,421, filed Mar. 12, 2004 now abandoned, and U.S. Provisional Application No. 60/454,527, filed Mar. 14, 2003, all of which are incorporated by reference herein in their entirety for any purpose.

The present invention comprises methods and formulations for treating at least one gastrointestinal condition in a subject in need thereof comprising administering to the subject a composition comprising a therapeutically effective amount of at least one α3 β4 nAChR antagonist or pharmaceutically acceptable salt thereof, wherein the at least one α3 β4 nAChR antagonist exhibits an $IC_{50}$ value for the α3 β4 sub-type of nAChR ranging from $1.0 \times 10^{-6}$ to $1 \times 10^{-9}$ or exhibits a potency for the α3 β4 nAChR sub-type at least two-times greater in comparison to at least one other nAChR sub-type. The present invention is further directed to a method of reducing gastrointestinal secretion in a subject suffering from an abnormal increase in gastrointestinal secretion comprising administering to the subject a gastrointestinal secretion reducing amount of N-2,3,3-tetramethylbicyclo-[2.2.1]heptan-2-amine, or a pharmaceutically acceptable salt thereof, wherein the N-2,3,3-tetramethylbicyclo-[2.2.1]heptan-2-amine, or a pharmaceutically acceptable salt thereof is administered in the form of a modified-release formulation.

In recent years, the molecular biology and pharmacology of the neuronal acetylcholine receptors (nAChR) have been investigated. These nAChRs are now recognized as a family of ligand-gated ion channels that by virtue of their tissue distribution and functional attributes, differentially modulate fast signal transmission at synapses on nervous, cardiovascular, immune, and neuromuscular systems. The nAChRs are named on the basis of their subunit components and are thought to have a pentameric functional motif formed from a variety of subunits. To date, eleven nAChR subunits (α2-9 and β2-4) have been identified. G. Kenneth Llyod and Michael Williams, *Neuronal Nicotinic Acetylcholine Receptors as Novel Drug Targets*, 292 J. Pharmacology & Experimental Therapeutics, 461-67 (2000).

Based on the stoichiometry and possible function of known native constructs of the nAChRs, putative targets for new drug therapies are being developed to exploit the action of these receptors. The focus of this work to date has been primarily directed to selective ligands at nAChR subtypes such as α4β2, α7 and α6β3 in relation to the treatment of various central nervous system (CNS) conditions such as cognitive impairment, neurodegenerative diseases such as Alzheimer disease, age associated memory impairment, pain, Parkinson disease, schizophrenia, depression and anxiety, epilepsy, attention-deficient/hyperactivity disorder (ADHD), smoking cessation, neurological conditions such as Tourette's syndrome, obesity, inflammation, and addiction (e.g., cocaine and alcohol). See id. at 464-66.

Some researches suggest a therapeutic benefit of nAChR based therapies in gastroenterology may be linked to the observation of reduced risk for ulcerative colitis in smokers and the suggestion that nicotinic agonists including nicotine itself may be of benefit. Id. at 466. To date, nicotinic agonists at nAChR sub-types have not been successfully developed to treat gastrointestinal (GI) disorders.

Targacept, a company specializing in the development of nAChR directed compounds, announced a program in October of 2002 for ulcerative colitis. U.S. Pat. No. 6,166,048 discloses potential benefits of nAChR directed agents to alter cytokine secretion and related inflammatory processes. This disclosure, however, does not link a particular nAChR sub-type to gastrointestinal conditions or the use of such a receptor to influence gut motility and/or diarrhea symptoms.

In fact, the effects of nAChR blocking drugs on gut function have been historically viewed in the art as an unwanted effects and linked with other peripheral actions such as effects on cardiovascular system, vision, bladder function, saliva, and sweat. Generally, those effects have been regarded as due to the "ganglion blocking effects." Laurence L. Brunton, John S. Lazo and Keith L. Parker, 9 Goodman & Gilman's The Pharmacological Basis of Therapeutics 181-84 (8th ed. 1990). For example, U.S. Patent Application Publication No. 2005/0033522 is directed to a computer system for generating molecular models of ligand-gated ion channels. That publication mentions the nAChR at α3 β4 subunit plays a role in cardiovascular and gastrointestinal action. However, such gastrointestinal action is directed to motility causing constipation, which is identified as "an undesirable side effect."

The present invention surprisingly provides that selective inhibition of the nAChR at α3 β4 containing subtype receptor (e.g., (α3)(β4)(αn) where n=0-9 such as n=5) achieves a selective effect on gut function without the traditional profile and incidence of other effects such as effects on cardiovascular system, vision, bladder function, saliva, and sweat.

The effect on gut function is to modify gut fluid and electrolyte secretion and for example, to decrease gut secretion, such as to decrease lower gut fluid content. In non-GI patients or subjects, that is demonstrated as a selective effect causing, e.g., constipation. The modifications to gut fluid and electrolyte secretion may also be accompanied by variations in gut motility.

GI conditions that will benefit from agents acting on the α3 β4 nAChR sub-type include conditions with increased or altered gut secretory function, which is normally associated with cancer-related diarrhea (e.g., colon cancer), carcinoid syndrome, chemotherapy and radiotherapy linked diarrhea, acquired immune deficiency syndrome (AIDS) related diarrhea, infectious diarrhea (such as bacterial and viral), food intolerance and malabsorption related diarrhea, medicine linked diarrhea including antibiotics, celiac disease, and endocrine diseases such as Addisons disease related diarrhea or conditions of an abnormal increased mixed secretory/motility basis such as irritable bowel syndrome (IBS) and further for example, diarrhea-related or linked symptoms, chronic diarrhea, functional diarrhea, diarrhea related symptoms of inflammatory bowel disease and microscopic colitis.

For example, mecamylamine HCl (N-2,3,3-tetramethylbicyclo[2.2.1]heptan-2-amine hydrochloride) is known in the art as a ganglionic blocking agent. Stone et al., *J. Pharm. Exp. Ther.*, 117(2), 169-183 (1956); Stone et al., *J. Med. Pharm. Chem.*, 5(4), 655-90 (1962). It is also recognized to cross the blood-brain barrier and function as a selective nicotinic-receptor antagonist. Papke et al., *J. Pharmacol. Exp. Ther.*, 297(2), 646-656 (2001). The compound has been used as a treatment for cardiovascular conditions, such as hypertension. Stone et al., *British Med. J.*, No. 5016, 422-425 (1957). It has also been used in the treatment of autonomic dysreflexia (Braddom et al., *Am. J. Phys. Med. Rehabil.*, 70(5), 234-240, 1991), as an aid in smoking cessation (Stolerman et al., *Pyschopharmacoliga*, 28, 247-259, 1973; Tennant et al., NIDA Res. Monograph, 291-297, 1984; Rose et al., Clin. Pharm. Ther., 56(1), 86-99, 1994; Rose et al., Exp. Clin. Pharmacol., 6(3), 331-343, 1998; Zevin et al., Clin Pham. & Therapeutics, 68(1), 58-66, 2000; and WO 0033812), as an aid in decreasing the dependence on cocaine (Reid et al., Neuropsychopharmacology, 20(3), 297-307, 1999), and has been investigated in the treatment of certain CNS conditions, such as Tourette's syndrome (Sandberg et al., Lancet, 352 (9129), 705-706, 1998; Young et al., Clinical Therapeutics, 23(4), 2001; Silver et al., Child and Adolescent Psych., 40(9), 1103-1110, 2001). Moreover, nothing is said regarding possible therapeutic benefits of mecamylamine's effect on gastrointestinal secretion or secretion/motility.

Additionally, United States Patent Application Publications 2002/0016370 and 2002/0016371 disclose the use of exo-(R)—N-2,3,3-tetramethylbicyclo[2.2.1]heptan-2-amine, or a pharmaceutically acceptable salt thereof, and exo-(S)—N-2,3,3-tetramethylbicyclo[2.2.1]heptan-2-amine, or a pharmaceutically acceptable salt thereof, respectively, for use in the treatment of medical conditions such as substance addiction, smoking cessation, hypertension, hypertensive crises, Tourette's syndrome and other tremors, cancer, atherogenic profile, neuropsychiatric disorders, chronic fatigue syndrome, Crohn's disease, autonomic dysreflexia, and spasmogenic intestinal disorders. Those publications, however, lack teachings directed to a particular receptor and using the pharmaceutical agent's affinity for a particular receptor to effect GI conditions. They also lack specificity as to what aspects or symptoms of those conditions may be treated and do not identify diarrhea-related symptoms as a particular target.

It is known that when mecamylamine hydrochloride is dosed orally using conventional formulations, the compound is nearly completely and rapidly absorbed from the gastrointestinal tract, leading to rapid attainment of a maximum plasma concentration. Bear et al., Am. J. Physiol., 186, 180-86 (1956). For example, Young et al. report that the administration of a 2.5 mg dose of mecamylamine hydrochloride to adults in a conventional formulation provides a maximum plasma concentration (Cmax) of about 7.89 ng/mL and a time to achieve the highest plasma concentration (Tmax) of 3.11 hours. Additionally, a 7.5 mg dose of mecamylamine hydrochloride to adults in a conventional formulation provides a Cmax of 23.68 ng/mL and a Tmax of 3.04 hours, so that the pharmacokinetic parameters are reported to be dose-proportional. Young et al., Clinical Therapeutics, 23(4) (2001). That report also shows that the average half-life of elimination of mecamylamine, dosed using conventional formulations, is about 10.1 hours to about 10.5 hours at either the 2.5 mg or 7.5 mg dose level. Although not reported by Young et al., one skilled in the art can calculate from that data that the expected ratio of peak plasma concentration of mecamylamine to plasma concentration of mecamylamine 24 hours after dosing would be about 4:1. Furthermore, it is expected that about 50% of the peak plasma concentration of mecamylamine would be maintained for about 14 hours, with the 24 hour plasma concentration level being less than about 25% of peak plasma concentration. The typical dose used for treating hypertensive subjects is about 25 mg/day, and is dosed using conventional formulations. From that dose, one skilled in the art would expect that the peak plasma concentration of mecamylamine would be about 78.9 ng/mL.

The once-daily administration of mecamylamine in this manner, however, provides plasma concentration levels that can cause undesirable side-effects, including impaired sexual function, cycloplegia, xerostomia, diminished perspiration, postural hypotension, hypothermia, tremors, anti-diuresis, antinociception, blurred vision, impotency, dysuria, tremor, choreiform movements, mental aberrations, nervousness, depression, anxiety, insomnia, slurred speech, weakness, fatigue, sedation, headache, constipation and renal insufficiency. Young et al., Clinical Therapeutics, 23(4) (2001). Despite the reported clinical utility of mecamylamine for treating cardiovascular conditions, autonomic dysreflexia, aiding in smoking cessation and decreasing the dependence on cocaine and certain CNS conditions such as Turette's syndrome, mecamylamine used in that traditional manner to treat GI conditions is dangerous because it still exerts it primary ganglion blocking effects resulting in unwanted side effects. Thus, a patient being treated with mecamylamine in a traditional manner for intestinal conditions will likely experience, for example, those side effects associated from its cardiovascular use of the drug. In addition, while the above discussed cited references have tangentially described mecamylamine's use in treating some intestinal conditions, none of these references has sought to target the receptor sub-type associated with such intestinal conditions in order to reduce, prevent and/or minimize the primary ganglion blocking effects.

To date, the art lacks an effective, safe and long-term treatment for gastrointestinal conditions such as cancer-related diarrhea, carcinoid syndrome, chemotherapy-related diarrhea, radiation-related diarrhea, AIDs related diarrhea, IBS and IBD. For instance, in the treatment of chemotherapy related diarrhea, only short-term use of loperamide (an opioid agent) is approved. However, for more refractory patients, the available therapy is limited to off-label use of octreotide (an injected peptide), which entails not only medical supervision but also, can be costly. Accordingly, an urgent need exists for new treatments of a variety of diarrhea related conditions that are both effective, convenient, safe and improve the subject's quality of life.

Figure 1:
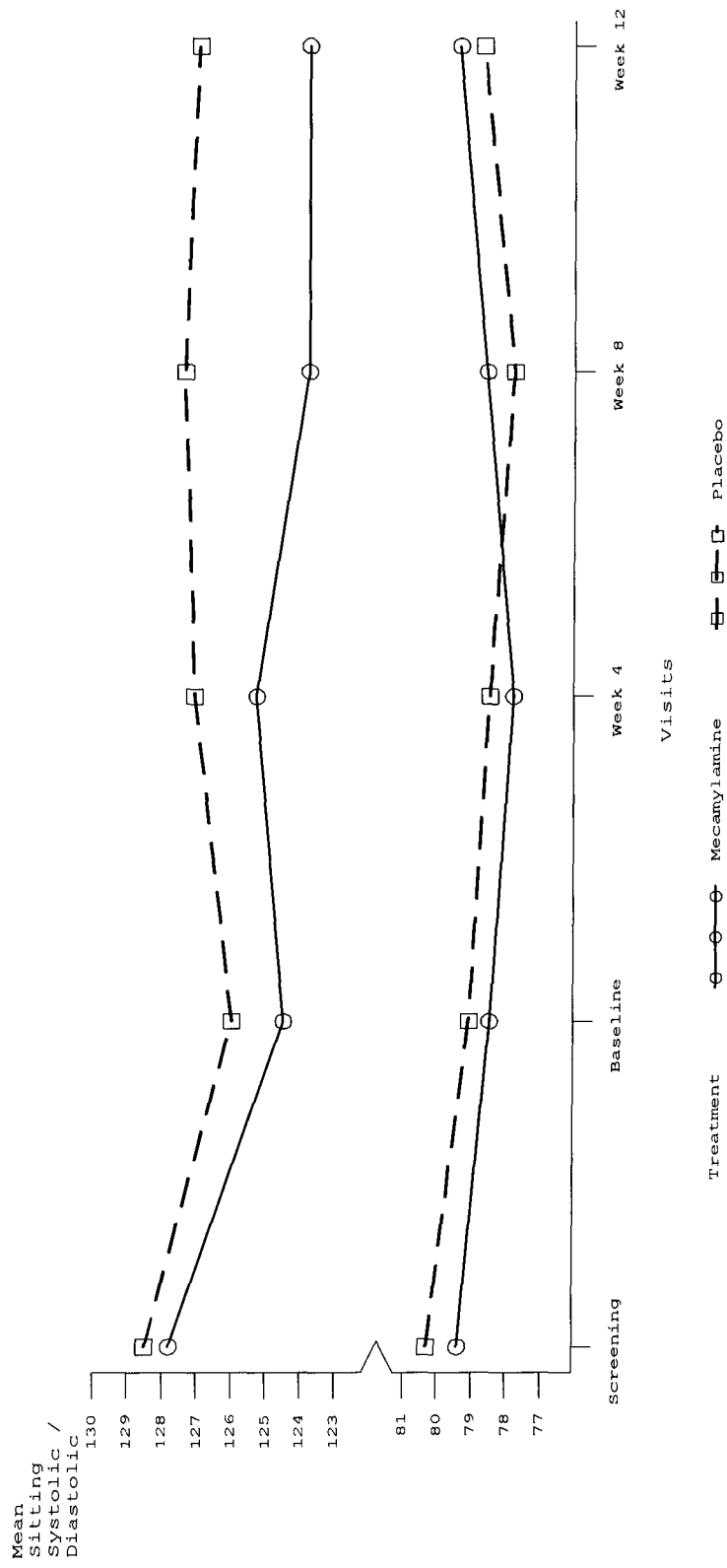
FIG. 1 is a graph of the mean sitting systolic/diastolic blood pressure provided in Example 3.

The present invention discloses methods for treating at least one gastrointestinal condition comprising administering a composition comprising a therapeutically effective amount of at least one α3 β4 nAChR antagonist or pharmaceutically acceptable salt thereof, wherein the composition is a modified release formulation and wherein the at least one α3 β4 antagonist exhibits an $IC_{50}$ value for the α3 β4 sub-type nAChR ranging from $1.0 \times 10^{-6}$ to $1 \times 10^{-9}$ or exhibits a potency for the α3 β4 sub-type of nAChR at least two times greater than other nAChR sub-types.

The present invention also provides methods for modifying and/or managing gut secretion in a subject in need thereof comprising administering to the subject a composition comprising a therapeutically effective amount of at least one α3 β4 nAChR antagonist or pharmaceutically acceptable salt thereof, wherein the composition is a modified-release formulation and wherein the at least one α3 β4 nAChR antagonist exhibits an IC50 value for the α3 β4 sub-type of nAChR ranging from $1.0 \times 10^{-6}$ to $1 \times 10^{-9}$ or exhibits a potency for the α3 β4 nAChR sub-type of nAChR at least two-times greater when compared to at least one other nAChR sub-type.

The present invention further provides methods for reducing gastrointestinal secretion in a subject suffering from an abnormal increase in gastrointestinal secretion comprising administering a composition comprising a therapeutically effective amount of N-2,3,3-tetramethylbicyclo-[2.2.1]heptan-2-amine or pharmaceutically acceptable salt thereof, wherein the composition is a modified-release formulation and wherein the N-2,3,3-tetramethylbicyclo-[2.2.1]heptan-2-amine exhibits an IC50 value for the α3 β4 sub-type of nAChR ranging from $1.0 \times 10^{-6}$ to $1 \times 10^{-9}$ or exhibits a potency for the α3 β4 nAChR sub-type of nAChR at least two-times greater when compared to at least one other nAChR sub-type.

The present invention still further provides for methods and formulations for reducing gastrointestinal secretions in a subject suffering from an abnormal increase in gastrointestinal secretion comprising administering to the subject a gastrointestinal secretion reducing amount of N-2,3,3-tetramethylbicyclo-[2.2.1]heptan-2-amine, or a pharmaceutically acceptable salt thereof, wherein the N-2,3,3-tetramethylbicyclo-[2.2.1]heptan-2-amine, or a pharmaceutically acceptable salt thereof is administered in the form of a modified-release formulation.

The present invention overcomes the deficiencies and problems in the prior art by selectively inhibiting the α3 β4 receptor sub-type of nAChR to achieve a selective effect on gut, i.e., gastrointestinal, function such as secretion thereby reducing, managing and/or preventing the incidence of other effects on the cardiovascular system, vision, bladder function, saliva and sweat and the traditional profiles exhibited when the at least one α3 β4 antagonist is used in a non-GI manner, e.g., mecamylamine used as a treatment for cardiovascular conditions.

The methods for treating, modifying, and/or managing fluctuations in gastrointestinal secretion (e.g., abnormal increases in fluid and electrolyte secretion) involve administering a composition comprising a therapeutically effective amount of at least one α3 β4 antagonist, or a pharmaceutically acceptable salt thereof, to a subject in need of such treatment, reduction, and/or management. Fluctuations in gastrointestinal secretion can be caused by at least one intestinal condition. Thus, the present invention can also be used to directly or indirectly reduce, prevent, and/or manage such intestinal conditions by decreasing gastrointestinal secretion.

Examples of intestinal conditions that can be treated, modified, and/or managed according to the present invention include, but are not limited to, diarrhea-related or linked symptoms, chronic diarrhea, functional diarrhea, cancer-related diarrhea (e.g., colon cancer), carcinoid syndrome, diarrhea related symptoms of inflammatory bowel disease and microscopic colitis, chemotherapy and radiotherapy linked diarrhea, AIDS related diarrhea, infectious diarrhea (such as bacterial and viral), food intolerance and malabsorption related diarrhea, medicine linked diarrhea including antibiotics, celiac disease, and endocrine diseases such as Addisons disease related diarrhea, or conditions of an increased mixed secretory/motility basis. Further for example, conditions of an increased secretory/motility basis can include, but not limited to, functional bowel disorders including irritable bowel syndrome (IBS), functional abdominal bloating, functional diarrhea, and unspecified functional bowel disorder; inflammatory bowel disease (IBD); ulcerative colitis; granulomatous enteritis; Crohn's disease; infectious diseases of the small and large intestine; pyloric spasm; abdominal cramps; mild dysenteries; diverticulitis; acute enterocolitis; neurogenic bowel disorders including the splenic flexure syndrome and neurogenic colon; spastic colitis; and/or symptoms of any of the foregoing. Those of ordinary skill in the art will be familiar with other types of intestinal and/or gastrointestinal conditions that produce abnormal changes in gastrointestinal secretory and/or motility, which can benefit from the present invention.

As used herein, the phrase "at least one α3 β4 antagonist" refers to at least one pharmaceutical agent that can act on nAChRs and be selective for the α3 β4 sub-type. For example, mecamylamine (N-2,3,3-tetramethylbicyclo-[2.2.1]heptan-2-amine) acts on nAChRs and in particular, the α3 β4 sub-type.

As used herein, the term "an abnormal increase in gastrointestinal secretion" refers to circumstances in which a subject experiences an increase in the secretion of fluid and electrolytes of the gastrointestinal tract due to a disease or an abnormal condition. Those conditions include, but are not limited to, diarrhea-related or linked symptoms, chronic diarrhea, functional diarrhea, cancer-related diarrhea (e.g., colon cancer), carcinoid syndrome, diarrhea related symptoms of inflammatory bowel disease and microscopic colitis, chemotherapy and radiotherapy linked diarrhea, AIDS related diarrhea, infectious diarrhea (such as bacterial and viral), food intolerance and malabsorption related diarrhea, medicine linked diarrhea including antibiotics, celiac disease, and endocrine diseases such as Addisons disease related diarrhea. Also included are those conditions or diseases which are currently unrecognized but display the same clinical symptoms of IBS, IBD, Crohn's disease, or ulcerative colitis, such as increases in gastrointestinal secretion, abdominal discomfort and audible bowel noises, cramping and abdominal pain, an urgency to defecate, the passage of loose stools covered with mucus, and diarrhea. Changes in gastrointestinal secretion according to the invention can be measured by any known method to those of ordinary skill in the art.

As used herein, the term "an increased secretory/motility basis" refers to a combination of not only an abnormal increase in gastrointestinal secretion but also increase in gastrointestinal motility such as circumstances in which a subject experiences an increase in the motility of the gastrointestinal tract due to a disease or an abnormal condition. Those disease and/or conditions can include, but are not limited to, those diseases that are currently recognized such as functional bowel disorders including irritable bowel syndrome (IBS), functional abdominal bloating, functional diarrhea, and unspecified functional bowel disorder; inflammatory bowel disease (IBD); ulcerative colitis; granulomatous enteritis; Crohn's disease; infectious diseases of the small and large intestine; pyloric spasm; abdominal cramps; mild dysenteries; diverticulitis; acute enterocolitis; neurogenic bowel disorders including the splenic flexure syndrome and neurogenic colon; spastic colitis; and/or symptoms of any of the foregoing.

As used herein, the term "N-2,3,3-tetramethylbicyclo-[2.2.1]heptan-2-amine" encompasses a pure stereoisomer of N-2,3,3-tetramethylbicyclo-[2.2.1]heptan-2-amine, such as pure exo-(R)—N-2,3,3-tetramethylbicyclo-[2.2.1]heptan-2-amine, exo-(S)—N-2,3,3-tetramethylbicyclo-[2.2.1]heptan-2-amine, endo-(R)—N-2,3,3-tetramethylbicyclo-[2.2.1]heptan-2-amine, and endo-(S)—N-2,3,3-tetramethylbicyclo-[2.2.1]heptan-2-amine, for example, or a mixture of any and all possible stereoisomers of N-2,3,3-tetramethylbicyclo-[2.2.1]heptan-2-amine, including exo-(R)—N-2,3,3-tetramethylbicyclo-[2.2.1]heptan-2-amine, exo-(S)—N-2,3,3-tetramethylbicyclo-[2.2.1]heptan-2-amine, endo-(R)—N-2,3,3-tetramethylbicyclo-[2.2.1]heptan-2-amine, and endo-(S)—N-2,3,3-tetramethylbicyclo-[2.2.1]heptan-2-amine, in any and all proportions, unless otherwise stated. Also included in this definition are mixtures of stereoisomers of N-2,3,3-tetramethylbicyclo-[2.2.1]heptan-2-amine in which two enantiomers, exo-(R)—N-2,3,3-tetramethylbicyclo-[2.2.1]heptan-2-amine and exo-(S)—N-2,3,3-tetramethylbicyclo-[2.2.1]heptan-2-amine for example, are present in equal amounts. Such mixtures are herein termed "racemic" compositions. Also included in this definition are mixtures comprising N-2,3,3-tetramethylbicyclo-[2.2.1]heptan-2-amine in which one stereoisomer is present in an amount greater than the others. For example, the mixture can comprise N-2,3,3-tetramethylbicyclo-[2.2.1]heptan-2-amine in which the exo-(R)—N-2,3,3-tetramethylbicyclo-[2.2.1]heptan-2-amine stereoisomer is present in an amount greater than the others. Such mixtures are herein termed "enriched (R)—N-2,3,3-tetramethylbicyclo-[2.2.1]heptan-2-amine" compositions. Alternatively, the mixture can comprise N-2,3,3-tetramethylbicyclo-[2.2.1]heptan-2-amine in which the exo-(S)—N-2,3,3-tetramethylbicyclo[2.2.1]heptan-2-amine stereoisomer is present in an amount greater than the others. Such formulations are herein termed "enriched (S)—N-2,3,3-tetramethylbicyclo-[2.2.1]heptan-2-amine" compositions. In addition, an enriched mixture can comprise N-2,3,3-tetramethylbicyclo-[2.2.1]heptan-2-amine in which the exo-(R)—N-2,3,3-tetramethylbicyclo-[2.2.1]heptan-2-amine stereoisomer the predominant isomer, present in an amount greater than or equal to ninety percent more than the others. Such mixtures are herein termed "substantially pure (R)—N-2,3,3-tetramethylbicyclo-[2.2.1]heptan-2-amine" compositions. Alternatively, an enriched mixture can comprise N-2,3,3-tetramethylbicyclo-[2.2.1]heptan-2-amine in which the exo-(S)—N-2,3,3-tetramethylbicyclo-[2.2.1]heptan-2-amine stereoisomer is present in an amount greater than or equal to ninety percent more than the others. Such formulations are herein termed "substantially pure (S)—N-2,3,3-tetramethylbicyclo-[2.2.1]heptan-2-amine" compositions. One skilled in the art will appreciate that "enriched" exo-(S)—N-2,3,3-tetramethylbicyclo-[2.2.1]heptan-2-amine encompasses "substantially pure" exo-(S)—N-2,3,3-tetramethylbicyclo-[2.2.1]heptan-2-amine. It is also contemplated that N-2,3,3-tetramethylbicyclo-[2.2.1]heptan-2-amine can be present as one or more pharmaceutically acceptable salts in any formulation of the invention.

As used herein, the term "modified-release" formulation or dosage form includes pharmaceutical preparations that achieve a desired release of the drug from the formulation. The term "modified-release" encompasses "extended-release" and "delayed-release" formulations, as well as formulations having both extended-release and delayed-release characteristics. The administration of a modified-release formulation to a subject can be designed to alter one of many pharmacokinetic parameters of a pharmaceutically active compound in a subject by influencing its release rate. Examples of such pharmacokinetic parameters include, but are not limited to, the maximum plasma concentration ($C_{max}$), the time to achieve a maximum plasma concentration following administration of the formulation ($T_{max}$), the area under the plasma concentration-time curve (AUC), peak:trough fluctuation ratio (also called the peak:trough plasma ratio, or Fluctuation Index (FI)), the apparent elimination half-life ($t_{1/2}$), the apparent rate of elimination ($K_{elim}$), the apparent clearance calculated as dose/AUC (Cl), and the apparent volume of distribution ($V_d$).

An "extended-release" formulation can extend the time during which a given plasma concentration of a pharmaceutically active compound is maintained or the time during which an influence or effect of a therapeutically effective dose of a pharmaceutically active compound is observed in a subject, relative to conventional formulations. Such formulations are referred to herein as "extended-release formulations."

A "delayed-release" formulation can be designed to delay the release of the pharmaceutically active compound for a specified period. Such formulations are referred to herein as "delayed-release" or "delayed-onset" formulations or dosage forms.

As used herein, the term "immediate-release formulation," is meant to describe those formulations comprising at least one the α3 β4 antagonist in which more than about 50% of the at least one the α3 β4 antagonist is released from the dosage form in less than about 2 hours. Such formulations are also referred to herein as "conventional formulations."

The methods and formulations of the present invention are meant to encompass those that contain all possible combinations of components that exhibit modified-release and a combination of modified-release and immediate-release properties. For example, a formulation and method of the invention can contain components that exhibit both extended-release and immediate-release properties, or both delayed-release and immediate-release properties, or both extended-release and delayed-release properties, or a combination of all three properties. For example, a formulation including both immediate-release and extended-release components can be combined in a capsule, which is then coated with an enteric coat to provide a delayed-release effect.

The present inventive formulations, i.e., compositions and methods are suitable for, but not limited to, oral, intra-nasal, buccal, sublingual, transdermal, and rectal administration, any of which can take the form of a modified-release or a combined modified-release and immediate-release formulation.

As used herein, the term "intra-nasal" administration refers to those modes of administering a compound to a subject by means of absorption through the mucous membranes of the nasal cavity, or any administration that is made through the nasal cavity.

As used herein, the term "oral" refers to those modes of administering a compound to a subject via the mouth. The term oral encompasses the terms "buccal administration" and "sublingual administration," which are meant to encompass those modes of administering a compound to a subject by means of absorption through the mucous membranes of the oral cavity, or any administration that is made where the drug is absorbed from the mouth.

As used herein, the term "transdermal administration" is meant to encompass those modes of administering a compound to a subject by means of absorption through the skin. The term "transdermal formulation" is meant to encompass those pharmaceutical formulations, devices, and modes of administration, that are suitable for the transdermal administration of a compound in a subject. Such formulations can include pharmaceutically inert carriers or agents that are suitable, in addition to a pharmaceutically active compound.

As used herein, the term "rectal administration" refers to those modes of administering a compound to a subject by means of absorption through the rectum. The term "rectal formulation" encompasses those pharmaceutical formulations that are suitable for the rectum such as a suppository and alternatively, the formulation may be provided as an enema.

As used herein, the term "pharmaceutically acceptable excipient" includes compounds that are compatible with the other ingredients in a pharmaceutical formulation and not injurious to the subject when administered in therapeutically acceptable amounts.

As used herein, the term "pharmaceutically acceptable salt" includes salts that are physiologically tolerated by a subject. Such salts can be prepared from an inorganic and/or organic acid. Examples of suitable inorganic acids include, but are not limited to, hydrochloric, hydrobromic, hydroiodic, nitric, sulfuric, and phosphoric acid. Organic acids can be aliphatic, aromatic, carboxylic, and/or sulfonic acids. Suitable organic acids include, but are not limited to, formic, acetic, propionic, succinic, camphorsulfonic, citric, fumaric, gluconic, lactic, malic, mucic, tartaric, para-toluenesulfonic, glycolic, glucuronic, maleic, furoic, glutamic, benzoic, anthranilic, salicylic, phenylacetic, mandelic, pamoic, methanesulfonic, ethanesulfonic, pantothenic, benzenesulfonic (besylate), stearic, sulfanilic, alginic, galacturonic, and the like.

The term "therapeutically effective amount," as used herein, refers to the amount of the at least one the α3 β4 antagonist, or a pharmaceutically acceptable salt thereof, which alone or in combination with other drugs, that is sufficient to reduce at least one symptom of conditions or diseases that cause an increase in gastrointestinal secretion, which include, but are not limited to, abdominal discomfort and audible bowel noises, cramping and abdominal pain, an urgency to defecate, the passage of loose stools covered with mucus, and diarrhea.

The term "side effects," as used herein refers to physiological effects observed in a subject following administration of at least one the α3 β4 antagonist, other than a change in gastrointestinal secretion, which may or may not result from an effect on the autonomic nervous system. For example, such effects include, but are not limited to, effects on a subject's heart rate, blood pressure, vision, and bladder function.

As used herein, the term "first administration" refers to the initial administration of a formulation of the invention to a subject. Alternatively, it refers to a single administration of a formulation of the invention to a subject.

In accordance with the invention, selective inhibition of the α3 β4 receptor sub-type by at least one the α3 β4 antagonist can achieve a selective effect on gut function such as secretion reducing and/or preventing the incidence of other effects such as on cardiovascular systems (e.g., blood pressure and heart rate), vision, bladder function, saliva, and sweat.

For example, mecamylamine has the following $IC_{50}$ values:

| Receptor | Racemic Mecamylamine | R-(−)- Mecamylamine | S-(+)- Mecamylamine |
|---|---|---|---|
| α3 β4 | 640-90 nM | 420-50 nM | 640-200 nM |
| α4 β2 | 2.5-0.6 μM | 1.7-0.5 μM | 3.2-0.5 μM |
| α3 β2 | 3.6-1.2 μM | 3.2-0.6 μM | 3.7-0.8 μM |
| α7 | 6.9-1.6 μM | 5.8-2.2 μM | 4.6-1.2 μM |
| α1 β1δε | N.A. | 1.1-0.3 μM | 2.2-0.6 μM |

N.A., not available.

Roger L. Papke et al., *Analysis of Mecamylamine Stereoisomers on Human Nicotinic Receptor Subtypes*, 297 J. Pharmacology & Experimental Therapeutics 646, 648 Table 1 (2001). From that data, mecamylamine exhibits a greater inhibition at α3 β4 receptors in view of other nAChR sub-types analyzed. For example, racemic mecamylamine at the α3 β4 receptor sub-type had an $IC_{50}$ value of 640-90 nM in contrast at the α4 β2 receptor sub-type, the $IC_{50}$ value was 2.5-0.6 μM; at α3 β2, the $IC_{50}$ value was 3.6-1.2 μM; and at α7, the $IC_{50}$ value was 6.9-1.6 μM. Both the R and S-stereoisomers of mecamylamine show similar $IC_{50}$ values at the α3 β4 receptor compared to the other receptors examined, i.e., α4 β2, α3 β2, α7, and α1 β1δε. Thus, mecamylamine (*racemic*, and R and S-*stereoisomers*) exhibits an $IC_{50}$ value for the α3 β4 sub-type of nAChR ranging from 10-7 to 10-9 and further for example, from 420-640 nM. In addition, mecamylamine exhibits a potency for the α3 β4 sub-type of nAChR at least two-times that of at least one of the other nAChR sub-type (compare racemic mecamylamine at the α3 β4 sub-type with an $IC_{50}$ value of 640-90 nM to the α4 β2 sub-type with an $IC_{50}$ value of 2.5-0.6 μM). In some embodiments, mecamylamine exhibits a potency for the α3 β4 sub-type of nAChR at least 2.5 times that of at least one of the other nAChR sub-type and in further embodiments, mecamylamine exhibits a potency for the α3 β4 sub-type of nAChR at least 3 times that of at least one of the other nAChR sub-type.

Given the potency differences between the receptor sub-types, mecamylamine evidences a selective inhibition of the α3 β4 receptor subtype. The comparison of $IC_{50}$ values for mecamylamine embodies at least one of the possible methods for determining whether a pharmaceutical compound is an α3 β4 antagonist.

Selective GI functionality (i.e., action at the α3 β4 sub-type of nAChR receptor system) versus general ganglion blocking effects can also be manipulated by the dose administered and the rate of delivery to a patient. For example, contrary to the traditional dosage of mecamylamine to treat hypertension of about 25 mg/day, the selective GI functionality of mecamylamine can be achieved at substantially lower daily doses, e.g., at a range from about 0.5 mg to about 10 mg, and further for example, at a range from about 1 mg to about 6 mg. In addition, by modifying the rate of absorption of the administered dose mecamylamine according to the present invention, lower peak plasma concentrations can be achieved in comparison to traditional mecamylamine dosages. Administering lower doses than traditional mecamylamine treatment as well as regulating rate of delivery provide for additional ways achieve selective GI functionality.

In addition, the methods of the present invention provide a peak:trough plasma level ratio of N-2,3,3-tetramethylbicyclo [2.2.1]heptan-2-amine of less than about 4:1, in some embodiments less than about 3:1, and in some embodiments less than about 2:1. As used herein with reference to peak: trough ratios, "peak" means the maximum plasma concentration, or $C_{max}$, and "trough" means the plasma level at 24 hours following a first administration, and during which the 24-hour period only one administration of a formulation of the invention is given to the subject.

The at least one α3 β4 antagonist in accordance with the present invention can be obtained by any method. For example, in at least one embodiment the at least one α3 β4 antagonist is mecamylamine, or a pharmaceutically acceptable salt there of and such methods are described in U.S. Pat. Nos. 2,831,027, 2,885,428, and 5,986,142, each of which is incorporated herein by reference for this purpose. Modifications of the protocols described in these patents, as well as other routes of synthesis, are well known to those of ordinary skill in the art and can be employed in accordance with the present invention.

Mixtures of any and all possible stereoisomers of N-2,3,3-tetramethylbicyclo-[2.2.1]heptan-2-amine, or pharmaceutically acceptable salts thereof, can be obtained by any method suitable for that purpose. For example, a racemic mixture of exo-(R)—N-2,3,3-tetramethylbicyclo-[2.2.1]heptan-2-amine and exo-(S)—N-2,3,3-tetramethylbicyclo-[2.2.1]heptan-2-amine, or pharmaceutically acceptable salts thereof, can be obtained by the methods disclosed in U.S. Pat. Nos. 2,831,027, 2,885,428, and 5,986,142. Enriched (R)—N-2,3,3-tetramethylbicyclo-[2.2.1]heptan-2-amine, enriched (S)—N-2,3,3-tetramethylbicyclo-[2.2.1]heptan-2-amine, substantially pure (R)—N-2,3,3-tetramethylbicyclo-[2.2.1]heptan-2-amine, or substantially pure (S)—N-2,3,3-tetramethylbicyclo-[2.2.1]heptan-2-amine or pharmaceutically acceptable salts thereof, can be obtained by the methods disclosed in U.S. Pat. No. 5,039,801 or U.S. Pat. App. Publication 20020016371 A1, for example.

The pharmaceutically acceptable formulations described herein can be provided in the form of a pharmaceutical formulation for use according to the present invention. Such formulations optionally include at least one pharmaceutically acceptable excipient. Examples of suitable excipients are known to those of skill in the art and are described, for example, in the *Handbook of Pharmaceutical Excipients* (Kibbe (ed.), 3$^{rd}$ Edition (2000), American Pharmaceutical Association, Washington, D.C.), and *Remington: The Science and Practice of Pharmacy* (Gennaro (ed.), 20$^{th}$ edition (2000), Mack Publishing, Inc., Easton, Pa.) (hereinafter referred to as "*Remington*"), both of which, for their disclosures relating to excipients and dosage forms, are incorporated herein by reference.

Suitable excipients include, but are not limited to, starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, plasticizers, gelling agents, thickeners, hardeners, setting agents, suspending agents, surfactants, humectants, carriers, stabilizers, antioxidants, and combinations thereof.

The pharmaceutical formulations of the invention can be provided in dosage forms that are suitable for administration to a subject by a desired route. A number of suitable dosage forms are described below, but this description is not meant to include all possible choices. One of skill in the art is familiar with the various dosage forms that are suitable for use in the present invention, as described, for example, in *Remington*, portions of which have been incorporated by reference above. The most suitable route in any given case will depend on the nature and severity of the condition being treated, modified, and/or managed. The pharmaceutical formulations of this invention can be formulated for administration orally, nasally, buccally, sublingually, rectally, intravaginally, parenterally, intracisternally, topically, and transdermally.

Formulations suitable for oral administration include, but are not limited to, capsules, cachets, pills, tablets, lozenges (using a flavored base, usually sucrose and acacia or tragacanth), powders, granules, solutions, suspensions in an aqueous or non-aqueous liquid, oil-in-water or water-in-oil liquid emulsions, elixirs, syrups, pastilles (using an inert base, such as gelatin and glycerin, or sucrose and acacia), mouth washes, pastes, and the like, each containing a predetermined amount of at least one α3 β4 antagonist, or a pharmaceutically acceptable salt thereof, to provide a therapeutic amount of the drug in one or more doses.

The at least one α3 β4 antagonist, or a pharmaceutically acceptable salt thereof, can be mixed with pharmaceutically acceptable excipients in the preparation of dosage forms for oral administration (capsules, tablets, pills, powders, granules and the like). Suitable excipients include, but are not limited to, carriers, such as sodium citrate or dicalcium phosphate; fillers or extenders, such as starches, lactose, sucrose, glucose, mannitol, or silicic acid; binders, such as hydroxymethyl-cellulose, alginates, gelatin, polyvinylpyrrolidone, sucrose or acacia; humectants, such as glycerol; disintegrating agents, such as agar, calcium carbonate, potato or tapioca starch, alginic acid, certain silicates, or sodium carbonate; solution retarding agents, such as paraffin; absorption accelerators, such as quaternary ammonium compounds; wetting agents, such as cetyl alcohol or glycerol monostearate; absorbents, such as kaolin and bentonite clay; lubricants, such as talc, calcium stearate, magnesium stearate, solid polyethylene glycols, and sodium lauryl sulfate; coloring agents; buffering agents; dispersing agents; preservatives; and diluents. The aforementioned excipients are given as examples only and are not meant to include all possible choices. Solid formulations can also be employed as fillers in soft and hard-filled gelatin capsules using excipients such as lactose or milk sugars, high molecular weight polyethylene glycols, and the like. Any of these dosage forms can optionally be scored or prepared with coatings and shells, such as enteric coatings and coatings for modifying the rate of release, examples of which are well known in the pharmaceutical-formulating art.

Such coatings can comprise sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, wax, or zein. In one embodiment, the coating material comprises hydroxypropyl methylcellulose. The coating material can further comprise anti-adhesives, such as talc; plasticizers (depending on the type of coating material selected), such as castor oil, diacetylated monoglycerides, dibutyl sebacate, diethyl phthalate, glycerin, polyethylene glycol, propylene glycol, triacetin, triethyl citrate; opacifiers, such as titanium dioxide; and/or coloring agents and/or pigments. The coating process can be carried out by any suitable means, for example, by using a perforated pan system such as the GLATT™, ACCELA-COTA™, and/or HICOATER™ apparatuses.

The formulations of the present invention can exist as a multiparticulate formulation. The term "multiparticulate" as used herein means a plurality of discrete or aggregated particles, beads, pellets, granules, tablets, or mixture thereof without regard to their size, shape, or morphology.

Tablets can be formed by any suitable process, examples of which are known to those of ordinary skill in the art. For example, the ingredients can be dry-granulated or wet-granulated by mixing in a suitable apparatus before being formed into tablets. Granules of the ingredients to be formed into tablets can also be prepared using suitable spray/fluidization or extrusion/spheronisation techniques.

The tablets can be formulated with suitable excipients to act as a fast dissolving and/or fast melting tablet in the oral cavity. Also, the tablet can be in the form of a chewable or effervescent dosage form. With effervescent dosage forms, the tablet can be added to a suitable liquid that causes it to disintegrate, dissolve, and/or disperse.

Tablets can be designed to have an appropriate hardness and friability to facilitate manufacture on an industrial scale using equipment to produce tablets at high speed. Also, the tablets can be packed or filled in any kind of container. It should be noted that the hardness of tablets, among other properties, can be influenced by the shape of the tablets. Different shapes of tablets can be used according to the present invention. Tablets can be circular, oblate, oblong, or any other shape. The shape of the tablets can also influence the disintegration rate.

Any of the inventive formulations can be encapsulated in soft and hard gelatin capsules, which can also include any of the excipients described above. For example, the encapsulated dosage form can include fillers, such as lactose and microcrystalline glidants, such as colloidal silicon dioxide and talc; lubricants, such as magnesium stearate; and disintegrating agents, such as starch (e.g., maize starch). Using capsule filling equipment, the ingredients to be encapsulated can be milled together, sieved, mixed, packed together, and then delivered into a capsule. Lubricants can be present in an amount of from about 0.5% (w/w) to about 2.0% (w/w). In one embodiment, the lubricant is about 1.25% (w/w) of the content of the capsule.

The formulations of the invention, which comprise at least one α3 β4 antagonist, or a pharmaceutically acceptable salt thereof, can also be formulated into a liquid dosage form for oral administration. Suitable formulations can include emulsions, microemulsions, solutions, suspensions, syrups, and elixirs. The at least one α3 β4 antagonist can be formulated as an ion-exchange resin complex, a microencapsulated particle, a liposome particle, or a polymer coated particle or granule. These formulations optionally include diluents commonly used in the art, such as, for example, water or other solvents, solubilizing agents and emulsifiers. Emulsifiers include, but are not limited to, ethyl alcohol, isopropyl alcohol, ethyl carbonate, ethyl acetate, benzyl alcohol, benzyl benzoate, propylene glycol, 1,3-butylene glycol, oils, glycerol, tetrahydrofurfuryl alcohol, polyethylene glycols, fatty acid esters of sorbitan, and mixtures thereof. In addition, the inventive formulations can include adjuvants such as wetting agents, emulsifying and suspending agents, sweetening, flavoring, coloring, perfuming, and preservative agents. Suitable suspension agents include, but are not limited to, ethoxylated isostearyl alcohols, polyoxyethylene sorbitol and sorbitan esters, microcrystalline cellulose, aluminum metahydroxide, bentonite, agar-agar and tragacanth, and mixtures thereof. The liquid formulations can be delivered as-is, or can be provided in hard or soft capsules, for example.

The amount of suspending agent present will vary according to the particular suspending agent used, and the presence or absence of other ingredients that have an ability to act as a suspending agent or contribute significantly to the viscosity of the formulation. The suspension can also contain ingredients that improve its taste, for example sweeteners; bitter-taste maskers, such as sodium chloride; taste-masking flavors, such as contramarum; flavor enhancers, such as monosodium glutamate; and flavoring agents. Examples of sweeteners include bulk sweeteners, such as sucrose, hydrogenated glucose syrup, the sugar alcohols sorbitol and xylitol; and sweetening agents such as sodium cyclamate, sodium saccharin, aspartame, and ammonium glycyrrhizinate. The liquid formulations can further comprise one or more buffering agents, as needed, to maintain a desired pH.

The liquid formulations of the present invention can also be filled into soft gelatin capsules. The liquid can include a solution, suspension, emulsion, microemulsion, precipitate, or any other desired liquid media carrying the pharmaceutically active compound. The liquid can be designed to improve the solubility of the pharmaceutically active compound upon release, or can be designed to form a drug-containing emulsion or dispersed phase upon release. Examples of such techniques are well known in the art. Soft gelatin capsules can be coated, as desired, with a functional coating. Such functional coatings generally serve the purpose of delaying the release of the drug for a predetermined period. For example, such coatings can allow the dosage form to pass through the stomach without being subjected to stomach acid or digestive juices. Thus, such coatings can dissolve or erode upon reaching a desired point in the gastrointestinal tract, such as the upper intestine.

The formulations of the present invention can also be provided in a form suitable for intra-nasal administration. The nasal delivery of therapeutic agents is known in the art. See, e.g., U.S. Pat. Nos. 4,428,883; 4,284,648; 4,394,390, and 4,77810, which are hereby incorporated by reference. The formulations of the invention suitable for intra-nasal administration comprise at least one α3 β4 antagonist, or a pharmaceutically acceptable salt thereof, and are in any form suitable for intra-nasal administration, including, but not limited to, gels, sprays and solutions which can be administered in the form of drops.

The formulations suitable for intra-nasal administration can be provided as isotonic aqueous solutions, suspensions, or viscous formulations, which can be buffered to a selected pH. The formulations can be in the form of gels, lotions, ointments, creams and the like and will typically contain a sufficient amount of a thickening agent so that the viscosity is from about 2500 to about 6500 cps, although more viscous formulations, even up to about 10,000 cps can be employed.

The concentration of the at least one α3 β4 antagonist in the formulations for intra-nasal administration can vary according to factors such as the condition being treated, the age, and the weight (or size) of the subject. The formulations of the invention can contain at least one α3 β4 antagonist, or a pharmaceutically acceptable salt thereof, in a concentration of from about 1 mg/mL to about 2000 mg/mL. The volume of a dosage unit can be from about 0.05 mL to about 0.3 mL.

The desired isotonicity of the formulation can be achieved using sodium chloride, or other pharmaceutically acceptable agents such as dextrose, boric acid, sodium tartrate, propylene glycol, or other inorganic or organic solutes.

The viscosity of the formulations can be maintained at the desired level using a pharmaceutically acceptable thickening agent. Suitable thickening agents include, but are not limited to, methyl cellulose, xanthan gum, carboxymethyl cellulose, hydroxypropyl cellulose, and carbomer.

Formulations suitable for intra-nasal administration can also contain a pharmaceutically acceptable humectant to inhibit drying of the mucous membrane and prevent irritation. Pharmaceutically acceptable humectants that can be used include, but are not limited to, sorbitol propylene glycol or glycerol. The concentration of the selected humectant will vary with the selected agent.

Enhanced absorption across the nasal membrane can be accomplished by employing a pharmaceutically acceptable surfactant. Pharmaceutically acceptable surfactants that can be used include, but are not limited to, polyoxyethylene derivatives of fatty acid partial esters of sorbitol anhydrides such as Tween 80, Polyoxyl 40 Stearate, Polyoxyethylene 50 Stearate and Octoxynol. These surfactants can be used in a range of from about 1% to about 10% based on the total weight of the formulation.

The intra-nasal formulations can also include a pharmaceutically acceptable preservative. Preservatives that can be used include, but are not limited to, benzyl alcohol, parabens, thimerosal, chlorobutanol, and benzalkonium chloride. These preservatives can be used in an amount ranging from about 0.02% to about 2%, based on the total weight of the formulation.

For buccal or sublingual administration, the formulations of the invention can be provided in the form of a tablet, patch, troche, or in free form, such as a gel, ointment, cream, or gum. Examples of suitable buccal or sublingual formulations and devices are disclosed, for example, in U.S. Pat. Nos. 5,863, 555, 5,849,322, 5,766,620, 5,516,523, 5,346,701, 4,983,395, and 4,849,224. Such formulations and devices can use a suitable adhesive to maintain the device in contact with the buccal mucosa. Examples of suitable adhesives are found, for example, in U.S. Pat. Nos. 3,972,995, 4,259,314, 4,680,323; 4,740,365, 4,573,996, 4,292,299, 4,715,369, 4,876,092, 4,855,142, 4,250,163, 4,226,848, and 4,948,580. Typically, the adhesive comprises a matrix of a hydrophilic, e.g., water soluble or swellable, polymer or mixture of polymers that can adhere to a wet, mucous surface. These adhesives can be formulated as ointments, thin films, tablets, troches, and other forms.

For rectal or vaginal administration, the inventive formulations can be provided as a suppository. Suppositories can comprise one or more non-irritating excipients such as, for example, polyethylene glycol, a suppository wax, or a salicylate. Such excipients can be selected on the basis of desirable physical properties. For example, a compound that is solid at room temperature but liquid at body temperature will melt in the rectum or vaginal cavity and release the active compound. The formulation can alternatively be provided as an enema for rectal delivery. Formulations suitable for vaginal administration also include pessaries, tampons, creams, gels, pastes, foams, or spray formulations containing such carriers, examples of which are known in the art.

Formulations suitable for topical or transdermal administration include, but are not limited to, powders, sprays, ointments, pastes, creams, lotions, gels, solutions, patches, and inhalants. Such formulations can contain excipients such as animal and vegetable fats, oils, waxes, paraffins, starch, tragacanth, cellulose derivatives, polyethylene glycols, silicones, bentonites, silicic acid, talc, zinc oxide, or mixtures thereof. Powders and sprays can also contain excipients such as lactose, talc, silicic acid, aluminum hydroxide, calcium silicates, and polyamide powder. Additionally, sprays can contain propellants, such as chlorofluoro-hydrocarbons and volatile unsubstituted hydrocarbons, such as butane and/or propane.

The systemic delivery of pharmaceutically active compounds via transdermal administration has the advantages of the accessibility of the skin as well as subject acceptability and compliance. In general, inventive transdermal delivery devices can be divided into categories, including, but not limited to, membrane-modulated, adhesive diffusion-controlled, matrix-dispersion-type, and microreservoir systems. See, *Remington*, Chapter 47, pp. 903-929, which, for the disclosure relating to transdermal delivery systems, is incorporated herein by reference.

For membrane-modulated systems, the drug reservoir is generally encapsulated in a shallow compartment molded from a drug-impermeable backing and a rate-controlling polymeric membrane. The at least one α3 β4 antagonist is released through the rate-controlling membrane, which can be microporous or nonporous. On the external surface of the membrane, a layer of drug-compatible, hypoallergenic, adhesive polymer can be applied to achieve contact of the delivery device with the subject's skin. Examples of the drug-compatible, hypoallergenic, adhesive polymer include, but are not limited to, silicone and polyacrylate adhesives. The rate of drug release can be altered by varying the polymer composition, permeability coefficient, or thickness of the rate-limiting membrane and adhesive.

In adhesive diffusion-controlled transdermal systems, the drug reservoir is generally formulated by directly dispersing the drug in an adhesive polymer matrix and spreading the dispersion onto a flat sheet of drug-impermeable backing to form a thin drug-reservoir layer. On top of this layer are placed further layers of non-drug containing adhesive polymers of constant thickness. The adhesive matrix can be prepared by mixing a solution of adhesive polymer, which can be purchased commercially, or by dissolving an adhesive solid in a suitable solvent, with a solution of at least one α3 β4 antagonist dissolved or evenly dispersed, in enhancers if desired. The mixture can be poured into a mold or cast alone or on a desired backing material. The casting can be left for the solvent to evaporate at room temperature or in an oven at a slightly elevated temperature. After solvent evaporation, the adhesive matrix takes the form of an adhesive polymer film, which can have a thickness in the range of about from 50 to 100 μm.

Matrix dispersion-type transdermal systems generally include drug reservoirs that are formed by dispersing a drug in a hydrophobic or lipophilic polymer and then molding it into a disk with a defined surface area and controlled thickness. Optionally, the drug may be homogenously dispersed. The disk can be glued onto an occlusive baseplate in a compartment prepared from a drug-impermeable backing. The adhesive polymer can be spread along the circumference of the disk to form a rim, which can then be applied to a subject's skin.

In microreservoir systems, the drug reservoir can be prepared by suspending the drug particles in an aqueous solution of water-soluble polymer and then dispersing it in a lipophilic polymer, for example, by high-shear mechanical force to form unleachable, microscopic spheres of drug. Optionally, the drug may be homogenously dispersed. The spheres are effective to release entrapped drug at a rate sufficient to achieve the desired skin permeation rate. Such particles can include a hydrophilic polymer chosen, for example, from polyvinyl alcohol, polyvinylpyrrilodone, polyacrylic acid, and celluloses. The particles can be liposomes. The dispersion is then stabilized by cross-linking the polymer in situ, producing a disk containing drug with a constant surface area and fixed thickness. The disk can then be positioned at the center of a transdermal system surrounded by an adhesive rim.

In transdermal formulations according to the invention, pharmaceutically active compounds can be present in any layers that comprise the transdermal delivery device. The amount of pharmaceutically active compounds present in each layer can be varied according to the desired rate of release for each. For example, an amount of the at least one α3 β4 antagonist loaded into the adhesive matrix can be varied by varying its concentration in the casting mixture and the thickness of the adhesive matrix. The amount of the at least one α3 β4 antagonist in the adhesive matrix of a given patch area should be sufficient to provide a gastrointestinal secretion reduction effect over the range of about 4 hours to about 7 days, or over the range of about 4 hours to about 72 hours, or over the range of about 4 to about 48 hours, or over the range of about 4 to about 24 hours, or any number of hours in between.

The transdermal devices according to the present invention can include at least one α3 β4 antagonist formulated and incorporated into the transdermal system in a microencapsulated or liposomal form. These forms can improve processing, stability, tolerability, or delivery characteristics of the system.

The transdermal devices according to the present invention can also include an enhancer effective to increase the skin permeation rate of the at least one α3 β4 antagonist. Enhancers that can be advantageously used to enhance the transdermal administration of the at least one α3 β4 antagonist include, but are not limited to, fatty acids, fatty acid esters, and fatty alcohols. Such compounds generally are hydrophobic or have limited water solubility, and the compounds can have a molecular weight of from about 150 to about 300 Daltons. Fatty alcohols include, but are not limited to, stearyl alcohol and oleyl alcohol. Fatty acids include, but are not limited to, oleic acid, lauric acid, myristic acid, palmitic acid, stearic acid, linoleic acid, caprylic acid, monoglycerides, diglycerides, acylcholines, caprylic acids, acylcarnitines, sodium caprate, and palmitoleic acid. Fatty acid esters containing 10, 11, 12 or more carbons can also be used. Examples of fatty acid esters include, but are not limited to, isopropyl myristate and methyl and ethyl esters of oleic and lauric acid.

Ionic enhancers can also be used. Ionic enhancers that can be used include, but are not limited to, sodium lauryl sulfate, sodium laurate, polyoxyethylene20-cetyether, laureth-9, sodium dodecylsulfate, and dioctyl sodium sulfosuccinate.

Bile salts can also be used. Bile salts that can be used include, but are not limited to, sodium glycocholate, sodium deoxycholate, sodium taurocholate, sodium taurodihydrofusidate, and sodium glycodihydrofusidate.

Chelating agents can also be used as enhancers Examples of chelating agents that can be used include, but are not limited to, EDTA, citric acid, and salicylates.

Another group of enhancers includes low molecular weight alcohols. Such alcohols can have a molecular weight of less than about 200 Daltons, or less than about 150 Daltons, or less than 100 Daltons. They can also be hydrophilic, generally having greater than 2 wt %, 5 wt %, or 10 wt % solubility in water at room temperature. Examples of such alcohols include, but are not limited to, methanol, ethanol, propanol, isopropanol, butanol, benzyl alcohol, glycerin, polyethylene glycol, propanediol, and propylene glycol.

Sulfoxides can also be used as enhancers. Examples of sulfoxides include, but are not limited to, dimethyl sulfoxide and decmethyl sulfoxide.

Other enhancers that can be used include, but are not limited to, urea and its derivatives, unsaturated cyclic ureas, 1-dodecylazacycloheptan-2-one, cyclodextrin, enamine derivatives, terpenes, liposomes, acyl carnitines, cholines, peptides (including polyarginine sequences or arginine rich sequences), peptidomimetics, diethyl hexyl phthalate, octyldodecyl myristate, isostearyl isostearate, caprylic/capric triglyceride, glyceryl oleate, and various oils (such as wintergreen or eucalyptol).

Other examples of enhancers suitable for use in the present invention are provided by Santus, G. C. et al., Journal of Controlled Release, 25:1-20 (1993), and *Remington*, both of which are incorporated by reference herein for their discussion of enhancers.

The adhesive used in an adhesive matrix-type transdermal patch can be selected from any adhesive acceptable for use in pharmaceutical patches. For example, an adhesive can be based on polyisobutylene, acrylics, or silicone. The adhesive selected can depend in part on the enhancer or enhancers chosen, and the amount of drug and enhancer loaded into the matrix. The adhesive should retain its adhesive properties in the presence of these additives, and provide tack for good instantaneous adhesion to the skin, good adhesion throughout the treatment period, and clean removal from the skin after treatment. Some suitable adhesives include those available from Avery Chemical Corp and from National Starch and Chemical Company.

Additionally, the transdermal patch of the invention can be used in combination with an energy-assisted device to enhance the delivery of the at least one $\alpha 3 \beta 4$ antagonist. Examples of such energy-assisted devices include, but are not limited to, iontophoretic, solar, and thermal devices.

In an iontophoresis drug delivery device, a battery can be connected to two electrodes in the device and the electrodes placed on the skin. The drug is placed in contact with one electrode (for example, a positive drug can be placed in contact with the positive electrode) and when a current of low voltage is applied across the electrodes, the drug will migrate through the skin toward the opposite electrode, thereby entering the body. The amount of drug delivered can be a function of the applied current and the treatment time, and these parameters are known to those of skill in the art. Iontophoresis and iontophoretic devices are discussed, for example, by Ranade et al, DRUG DELIVERY SYSTEMS, CRC Press, Chapter 6, (1996); Tyle, Pharmaceutical Res., 3:318 (1986); and Banga et al., J. Controlled Release, 7:1-24 (1988), each of which is incorporated by reference herein for their discussion of iontophoresis and iontophoretic devices.

The release profiles and skin permeation rates of the transdermal formulations of the present invention can be determined using an in vitro diffusion test according to methods adapted from Franz, J. Invest. Dermatol. 64:194-195 (1975) and GB-A-2 098 865.

For parenteral administration, such as administration by injection (including, but not limited to, subcutaneous, bolus injection, intramuscular, intraperitoneal, and intravenous), the pharmaceutical formulations can be formulated as isotonic suspensions, solutions, or emulsions, in oily or aqueous vehicles, and can contain formulatory agents such as suspending, stabilizing, or dispersing agents. Alternatively, the formulations can be provided in dry form such as a powder, crystalline, or freeze-dried solid, for reconstitution with sterile pyrogen-free water or isotonic saline before use. They can be presented, for example, in sterile ampoules or vials.

Examples of suitable aqueous and nonaqueous excipients include water, ethanol, polyols (such as glycerol, propylene glycol, polyethylene glycol, and the like), oils, injectable organic esters, and mixtures thereof. Proper fluidity can be maintained, for example, by the use of surfactants.

These formulations can also contain adjuvants such as preservatives, wetting agents, emulsifying agents, and dispersing agents. Prevention of the action of microorganisms can be achieved by the inclusion of various antibacterial and/or antifungal agents, for example, paraben, chlorobutanol, phenol sorbic acid, and the like. It also can be desirable to include isotonic agents, such as sugars, sodium chloride, and the like in the formulations. In addition, prolonged absorption of the injectable pharmaceutical form can be brought about by the inclusion of agents that delay absorption, such as aluminum monostearate and/or gelatin.

To prolong or extend the therapeutic effect of a drug, it can be desirable to slow the absorption of the drug from a subcutaneous or intramuscular injection. This can be accomplished by the use of a liquid suspension of crystalline or amorphous material having low solubility. Alternatively, modified release of injected forms can be achieved by encapsulation of at least one $\alpha 3 \beta 4$ antagonist in a biodegradable or biocompatible polymer that controls the rate of drug release. Alternatively, liposome formulations can be used. The rate of absorption of the drug then generally depends upon its rate of dissolution, which can depend upon crystal size and crystalline form. Alternatively, delayed absorption of a parenterally-administered form can be accomplished by dissolving or suspending the drug in an oil vehicle.

In addition to the inventive dosage forms described herein, the formulations of the present invention can be formulated into an oral dosage form that modifies the release of the at least one $\alpha 3 \beta 4$ antagonist. Examples of modified-release formulations are known in the art and are, for example, described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566. Advantages of modified-release formulations can include extended activity of the drug, reduced dosage frequency, and increased subject compliance.

A number of modified dosage forms suitable for use are described below. A more detailed discussion of such forms can also be found in, for example *The Handbook of Pharmaceutical Controlled Release Technology*, D. L. Wise (ed.), Marcel Decker, Inc., New York (2000); and also in *Treatise on Controlled Drug Delivery: Fundamentals, Optimization, and Applications*, A. Kydonieus (ed.), Marcel Decker, Inc., New York, (1992), the relevant contents of each of which are hereby incorporated by reference for this purpose.

Examples of modified or extended-release formulations include but are not limited to, diffusion-controlled, matrix, osmotic, and ionic exchange systems. These can be in the form of single (monolithic) or multiunit dosage forms. With diffusion-controlled extended release dosage forms, the formulation containing the active substance of interest can be surrounded by a semi-permeable membrane. Semi-permeable membranes include those that are permeable to a greater or lesser extent to both water and solute. This membrane can include water-insoluble and/or water-soluble polymers, and can exhibit pH-dependent and/or pH-independent solubility characteristics. Polymers of these types are described in detail below. Generally, the characteristics of the polymeric membrane (e.g., the composition of the membrane) will determine the nature of release from the dosage form.

Matrix-Based Dosage Forms

Matrix-type systems comprise an active substance of interest, mixed with either water-soluble, e.g., hydrophilic polymers, or water-insoluble, e.g., hydrophobic polymers. Generally, the properties of the polymer used in a modified-release dosage form will affect the mechanism of release. For example, the release of the active ingredient from a dosage form containing a hydrophilic polymer can proceed via both surface diffusion and/or erosion. Mechanisms of release from pharmaceutical systems are well known to those skilled in the art. Matrix-type systems can also be monolithic or multiunit, and can be coated with water-soluble and/or water-insoluble polymeric membranes, examples of which are described above.

Matrix formulations of the present invention can be prepared by using, for example, direct compression or wet granulation. A functional coating, as noted above, can then be applied in accordance with the invention. Additionally, a barrier or sealant coat can be applied over a matrix tablet core prior to application of a functional coating. The barrier or sealant coat can serve the purpose of separating an active ingredient from a functional coating, which can interact with the active ingredient, or it can prevent moisture from contacting the active ingredient. Details of barriers and sealants are provided below.

In a matrix-based dosage form in accordance with the present invention, the at least one $\alpha 3$ $\beta 4$ antagonist and optional pharmaceutically acceptable excipient(s) are dispersed within a polymeric matrix, which typically comprises one or more water-soluble polymers and/or one or more water-insoluble polymers. The drug can be released from the dosage form by diffusion and/or erosion. Such matrix systems are described in detail by Wise and Kydonieus, supra.

Suitable water-soluble polymers include, but are not limited to, polyvinyl alcohol, polyvinylpyrrolidone, methylcellulose, hydroxypropylcellulose, hydroxypropylmethyl cellulose, or polyethylene glycol, and/or mixtures thereof.

Suitable water-insoluble polymers include, but are not limited to, ethylcellulose, cellulose acetate, cellulose propionate, cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(ethylene oxide), poly(ethylene terephthalate), poly(vinyl isobutyl ether), poly(vinyl acetate), poly(vinyl chloride), and polyurethane, and/or mixtures thereof.

Suitable pharmaceutically acceptable excipients include, but are not limited to, carriers, such as sodium citrate and dicalcium phosphate; fillers or extenders, such as stearates, silicas, gypsum, starches, lactose, sucrose, glucose, mannitol, talc, and silicic acid; binders, such as hydroxypropyl methylcellulose, hydroxymethyl-cellulose, alginates, gelatin, polyvinyl pyrrolidone, sucrose, and acacia; humectants, such as glycerol; disintegrating agents, such as agar, calcium carbonate, potato and tapioca starch, alginic acid, certain silicates, EXPLOTAB™, crospovidone, and sodium carbonate; solution retarding agents, such as paraffin; absorption accelerators, such as quaternary ammonium compounds; wetting agents, such as cetyl alcohol and glycerol monostearate; absorbents, such as kaolin and bentonite clay; lubricants, such as talc, calcium stearate, magnesium stearate, solid polyethylene glycols, and sodium lauryl sulfate; stabilizers, such as fumaric acid; coloring agents; buffering agents; dispersing agents; preservatives; organic acids; and organic bases. The aforementioned excipients are given as examples only and are not meant to include all possible choices. Additionally, many excipients can have more than one role or function, or can be classified in more than one group; the classifications are descriptive only, and are not intended to limit any use of a particular excipient.

For example, a matrix-based dosage form can comprise at least one $\alpha 3$ $\beta 4$ antagonist; a filler, such as starch, lactose, or microcrystalline cellulose (AVICEL™); a binder/controlled-release polymer, such as hydroxypropyl methylcellulose or polyvinyl pyrrolidone; a disintegrant, such as EXPLOTAB™, crospovidone, or starch; a lubricant, such as magnesium stearate or stearic acid; a surfactant, such as sodium lauryl sulfate or polysorbates; and a glidant, such as colloidal silicon dioxide (AEROSIL™) or talc.

The amounts and types of polymers, and the ratio of water-soluble polymers to water-insoluble polymers in the inventive formulations are generally selected to achieve a desired release profile of at least one $\alpha 3$ $\beta 4$ antagonist, as described below. For example, by increasing the amount of water insoluble-polymer relative to the amount of water soluble-polymer, the release of the drug can be delayed or slowed. This is due, in part, to an increased impermeability of the polymeric matrix, and, in some cases, to a decreased rate of erosion during transit through the gastrointestinal tract.

Osmotic Pump Dosage Forms

In another embodiment, the modified release formulations of the present invention are provided as osmotic pump dosage forms. In an osmotic pump dosage form, a core containing at least one $\alpha 3$ $\beta 4$ antagonist and optionally one or more osmotic excipients is typically encased by a selectively permeable membrane having at least one orifice. The selectively permeable membrane is generally permeable to water, but impermeable to the drug. When the system is exposed to body fluids, water penetrates through the selectively permeable membrane into the core containing the drug and optional osmotic excipients. The osmotic pressure increases within the dosage form. Consequently, the drug is released through the orifice(s) in an attempt to equalize the osmotic pressure across the selectively permeable membrane.

In more complex pumps, the dosage form can contain two internal compartments in the core. The first compartment contains the drug and the second compartment can contain a polymer, which swells on contact with aqueous fluid. After ingestion, this polymer swells into the drug-containing compartment, diminishing the volume occupied by the drug, thereby delivering the drug from the device at a controlled rate over an extended period of time. Such dosage forms are often used when a zero order release profile is desired.

Osmotic pumps are well known in the art. For example, U.S. Pat. Nos. 4,088,864, 4,200,098, and 5,573,776, each of which is hereby incorporated by reference for this purpose, describe osmotic pumps and methods of their manufacture. The osmotic pumps useful in accordance with the present invention can be formed by compressing a tablet of an osmotically active drug, or an osmotically inactive drug in combination with an osmotically active agent, and then coating the tablet with a selectively permeable membrane which is permeable to an exterior aqueous-based fluid but impermeable to the drug and/or osmotic agent.

At least one delivery orifice can be drilled through the selectively permeable membrane wall. Alternatively, at least one orifice in the wall can be formed by incorporating leachable pore-forming materials in the wall. In operation, the exterior aqueous-based fluid is imbibed through the selectively permeable membrane wall and contacts the drug to form a solution or suspension of the drug. The drug solution or suspension is then pumped out through the orifice as fresh fluid is imbibed through the selectively permeable membrane.

Typical materials for the selectively permeable membrane include selectively permeable polymers known in the art to be useful in osmosis and reverse osmosis membranes, such as cellulose acylate, cellulose diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethyl aminoacetate, cellulose acetate ethyl carbamate, cellulose acetate chloracetate, cellulose dipalmitate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, lightly cross-linked polystyrene derivatives, cross-linked poly(sodium styrene sulfonate), poly(vinylbenzyltrimethyl ammonium chloride), cellulose acetate, cellulose diacetate, cellulose triacetate, and/or mixtures thereof.

The osmotic agents that can be used in the pump are typically soluble in the fluid that enters the device following administration, resulting in an osmotic pressure gradient across the selectively permeable wall against the exterior fluid. Suitable osmotic agents include, but are not limited to, magnesium sulfate, calcium sulfate, magnesium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, glucose, hydrophilic polymers such as cellulose polymers, and/or mixtures thereof.

As discussed above, the osmotic pump dosage form can contain a second compartment containing a swellable polymer. Suitable swellable polymers typically interact with water and/or aqueous biological fluids, which causes them to swell or expand to an equilibrium state. Acceptable polymers exhibit the ability to swell in water and/or aqueous biological fluids, retaining a significant portion of such imbibed fluids within their polymeric structure, so as to increase the hydrostatic pressure within the dosage form. The polymers can swell or expand to a very high degree, usually exhibiting a 2- to 50-fold volume increase. The polymers can be non-cross-linked or cross-linked. In one embodiment, the swellable polymers are hydrophilic polymers.

Suitable polymers include, but are not limited to, poly (hydroxy alkyl methacrylate) having a molecular weight of from 30,000 to 5,000,000 Daltons; kappa-carrageenan; polyvinylpyrrolidone having a molecular weight of from 10,000 to 360,000 Daltons; anionic and cationic hydrogels; polyelectrolyte complexes; poly(vinyl alcohol) having low amounts of acetate, cross-linked with glyoxal, formaldehyde, or glutaraldehyde, and having a degree of polymerization from 200 to 30,000 Daltons; a mixture including methyl cellulose, cross-linked agar and carboxymethyl cellulose; a water-insoluble, water-swellable copolymer produced by forming a dispersion of finely divided maleic anhydride with styrene, ethylene, propylene, butylene, or isobutylene; water-swellable polymers of N-vinyl lactams; and/or mixtures of any of the foregoing.

The term "orifice" as used herein comprises means and methods suitable for releasing the drug from the dosage form. The expression includes one or more apertures or orifices that have been bored through the selectively permeable membrane by mechanical procedures. Alternatively, an orifice can be formed by incorporating an erodible element, such as a gelatin plug, in the selectively permeable membrane. In such cases, the pores of the selectively permeable membrane form a "passageway" for the passage of the drug. Such "passageway" formulations are described, for example, in U.S. Pat. Nos. 3,845,770 and 3,916,899, the relevant disclosures of which are incorporated herein by reference for this purpose.

The osmotic pumps useful in accordance with this invention can be manufactured by known techniques. For example, the drug and other ingredients can be milled together and pressed into a solid having the desired dimensions (e.g., corresponding to the first compartment). The swellable polymer is then formed, placed in contact with the drug, and both are surrounded with the selectively permeable agent. If desired, the drug component and polymer component can be pressed together before applying the selectively permeable membrane. The selectively permeable membrane can be applied by any suitable method, for example, by molding, spraying, or dipping.

Membrane-Modified Dosage Forms

The modified release formulations of the present invention can also be provided as membrane-modified formulations. Membrane-modified formulations of the present invention can be made by preparing a rapid release core, which can be a monolithic (e.g., tablet) or multi-unit (e.g., pellet) type, and coating the core with a membrane. The membrane-modified core can then be further coated with a functional coating. In between the membrane-modified core and functional coating, a barrier or sealant can be applied. Details of membrane-modified dosage forms are provided below.

For example, the at least one α3 β4 antagonist can be provided in a multiparticulate membrane-modified formulation. The at least one α3 β4 antagonist can be formed into an active core by applying the compound to a nonpareil seed having an average diameter in the range of about 0.4 to about 1.1 mm or about 0.85 to about 1.00 mm. The at least one α3 β4 antagonist can be applied with or without additional excipients onto the inert cores, and can be sprayed from solution or suspension using a fluidized bed coater (e.g., Wurster coating) or pan coating system. Alternatively, they can be applied as a powder onto the inert cores using a binder to bind the at least one α3 β4 antagonist onto the cores. Active cores can also be formed by extrusion of the core with suitable plasticizers (described below) and any other processing aids as necessary.

The modified-release formulations of the present invention comprise at least one polymeric material, which is applied as a membrane coating to the drug-containing cores. Suitable water-soluble polymers include, but are not limited to, polyvinyl alcohol, polyvinylpyrrolidone, methylcellulose, hydroxypropylcellulose, hydroxypropylmethyl cellulose, polyethylene glycol, and/or mixtures thereof.

Suitable water-insoluble polymers include, but are not limited to, ethylcellulose, cellulose acetate, cellulose propionate, cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), and poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(ethylene oxide), poly(ethylene terephthalate), poly(vinyl isobutyl ether), poly(vinyl acetate), poly(vinyl chloride), polyurethane, and/or mixtures thereof.

EUDRAGIT™ polymers (available from Rohm Pharma) are polymeric lacquer substances based on acrylates and/or methacrylates. A suitable polymer that is freely permeable to the active ingredient and water is EUDRAGIT™ RL. A suitable polymer that is slightly permeable to the active ingredient and water is EUDRAGIT™ RS. Other suitable polymers that are slightly permeable to the active ingredient and water, and exhibit a pH-dependent permeability include, but are not limited to, EUDRAGIT™ L, EUDRAGIT™ S, and EUDRAGIT™ E.

EUDRAGIT™ RL and RS are acrylic resins comprising copolymers of acrylic and methacrylic acid esters with a low content of quaternary ammonium groups. The ammonium groups are present as salts and give rise to the permeability of the lacquer films. EUDRAGIT™ RL and RS are freely permeable (RL) and slightly permeable (RS), respectively, independent of pH. The polymers swell in water and digestive juices, in a pH-independent manner. In the swollen state, they are permeable to water and to dissolved active compounds.

EUDRAGIT™ L is an anionic polymer synthesized from methacrylic acid and methacrylic acid methyl ester. It is insoluble in acids and pure water. It becomes soluble in neutral to weakly alkaline conditions. The permeability of EUDRAGIT™ L is pH dependent. Above pH 5.0, the polymer becomes increasingly permeable.

In one embodiment comprising a membrane-modified dosage form, the polymeric material comprises methacrylic acid co-polymers, ammonio methacrylate co-polymers, or a mixture thereof. Methacrylic acid co-polymers such as EUDRAGIT™ S and EUDRAGIT™ L (Rohm Pharma) are particularly suitable for use in the modified release formulations of the present invention. These polymers are gastroresistant and enterosoluble polymers. Their polymer films are insoluble in pure water and diluted acids. They dissolve at higher pHs, depending on their content of carboxylic acid. EUDRAGIT™ S and EUDRAGIT™ L can be used as single components in the polymer coating or in combination in any ratio. By using a combination of the polymers, the polymeric material can exhibit a solubility at a pH between the pHs at which EUDRAGIT™ L and EUDRAGIT™ S are separately soluble.

The membrane coating can comprise a polymeric material comprising a major proportion (i.e., greater than 50% of the total polymeric content) of one or more pharmaceutically acceptable water-soluble polymers, and optionally a minor proportion (i.e., less than 50% of the total polymeric content) of one or more pharmaceutically acceptable water-insoluble polymers. Alternatively, the membrane coating can comprise a polymeric material comprising a major proportion (i.e., greater than 50% of the total polymeric content) of one or more pharmaceutically acceptable water-insoluble polymers, and optionally a minor proportion (i.e., less than 50% of the total polymeric content) of one or more pharmaceutically acceptable water-soluble polymers.

Ammonio methacrylate co-polymers such as EUDRAGIT™ RS and EUDRAGIT™ RL are suitable for use in the modified release formulations of the present invention. These polymers are insoluble in pure water, dilute acids, buffer solutions, or digestive fluids over the entire physiological pH range. The polymers swell in water and digestive fluids independently of pH. In the swollen state they are then permeable to water and dissolved actives. The permeability of the polymers depends on the ratio of ethylacrylate (EA), methyl methacrylate (MMA), and trimethylammonioethyl methacrylate chloride (TAMCl) groups in the polymer. Those polymers having EA:MMA:TAMCl ratios of 1:2:0.2 (EUDRAGIT™ RL) are more permeable than those with ratios of 1:2:0.1 (EUDRAGIT™ RS). Polymers of EUDRAGIT™ RL are insoluble polymers of high permeability. Polymers of EUDRAGIT™ RS are insoluble films of low permeability.

The ammonio methacrylate co-polymers can be combined in any desired ratio. For example, a ratio of EUDRAGIT™ RS:EUDRAGIT™ RL (90:10) can be used. The ratios can furthermore be adjusted to provide a delay in release of the drug. For example, the ratio of EUDRAGIT™ RS:EUDRAGIT™ RL can be about 100:0 to about 80:20, about 100:0 to about 90:10, or any ratio in between. In such formulations, the less permeable polymer EUDRAGIT™ RS would generally comprise the majority of the polymeric material.

The ammonio methacrylate co-polymers can be combined with the methacrylic acid co-polymers within the polymeric material in order to achieve the desired delay in release of the drug. Ratios of ammonio methacrylate co-polymer (e.g., EUDRAGIT™ RS) to methacrylic acid co-polymer in the range of about 99:1 to about 20:80 can be used. The two types of polymers can also be combined into the same polymeric material, or provided as separate coats that are applied to the core.

In addition to the EUDRAGIT™ polymers described above, a number of other such copolymers can be used to control drug release. These include methacrylate ester co-polymers (e.g., EUDRAGIT™ NE 30D). Further information on the EUDRAGIT™ polymers can be found in "Chemistry and Application Properties of Polymethacrylate Coating Systems," in *Aqueous Polymeric Coatings for Pharmaceutical Dosage Forms* (ed. James McGinity, Marcel Dekker Inc., New York, pg 109-114).

The coating membrane can further comprise at least one soluble excipient so as to increase the permeability of the polymeric material. Suitably, the soluble excipient is selected from among a soluble polymer, a surfactant, an alkali metal salt, an organic acid, a sugar, and a sugar alcohol. Such soluble excipients include, but are not limited to, polyvinyl pyrrolidone, polyethylene glycol, sodium chloride, surfactants such as sodium lauryl sulfate and polysorbates, organic acids such as acetic acid, adipic acid, citric acid, fumaric acid, glutaric acid, malic acid, succinic acid, and tartaric acid, sugars such as dextrose, fructose, glucose, lactose and sucrose, sugar alcohols such as lactitol, maltitol, mannitol, sorbitol and xylitol, xanthan gum, dextrins, and maltodextrins. In some embodiments, polyvinyl pyrrolidone, mannitol, and/or polyethylene glycol can be used as soluble excipients. The soluble excipient(s) can be used in an amount of from about 1% to about 10% by weight, based on the total dry weight of the polymer.

In another embodiment, the polymeric material comprises at least one water-insoluble polymers, which is also insoluble in gastrointestinal fluids, and at least one water-soluble pore-forming compound. For example, the water-insoluble polymer can comprise a terpolymer of polyvinylchloride, polyvinylacetate, and/or polyvinylalcohol. Suitable water-soluble pore-forming compounds include, but are not limited to, saccharose, sodium chloride, potassium chloride, polyvinylpyrrolidone, and/or polyethyleneglycol. The pore-forming compounds can be uniformly or randomly distributed throughout the water-insoluble polymer. Typically, the pore-forming compounds comprise about 1 part to about 35 parts for each about 1 to about 10 parts of the water-insoluble polymers.

When such dosage forms come in to contact with the dissolution media (e.g., intestinal fluids), the pore-forming compounds within the polymeric material dissolve to produce a porous structure through which the drug diffuses. Such formulations are described in more detail in U.S. Pat. No. 4,557,925, which relevant part is incorporated herein by reference for this purpose. The porous membrane can also be coated with an enteric coating, as described herein, to inhibit release in the stomach.

For example, a pore-forming modified-release dosage form can comprise at least one α3 β4 antagonist; a filler, such as starch, lactose, or microcrystalline cellulose (AVICEL™); a binder/modified release polymer, such as hydroxypropyl methylcellulose or polyvinyl pyrrolidone; a disintegrant, such as, EXPLOTAB™, crospovidone, or starch; a lubricant, such as magnesium stearate or stearic acid; a surfactant, such as sodium lauryl sulphate or polysorbates; and a glidant, such as colloidal silicon dioxide (AEROSIL™) or talc.

The polymeric material can also include at least one auxiliary agents such as fillers, plasticizers, and/or anti-foaming agents. Representative fillers include talc, fumed silica, glyceryl monostearate, magnesium stearate, calcium stearate, kaolin, colloidal silica, gypsum, micronized silica, and magnesium trisilicate. The quantity of filler used typically ranges from about 2% to about 300% by weight, and can range from about 20% to about 100%, based on the total dry weight of the polymer. In one embodiment, talc is the filler.

The coating membranes, and functional coatings as well, can also include a material that improves the processing of the polymers. Such materials are generally referred to as plasticizers and include, for example, adipates, azelates, benzoates, citrates, isoebucates, phthalates, sebacates, stearates, and glycols. Representative plasticizers include acetylated monoglycerides, butyl phthalyl butyl glycolate, dibutyl tartrate, diethyl phthalate, dimethyl phthalate, ethyl phthalyl ethyl glycolate, glycerin, ethylene glycol, propylene glycol, triacetin citrate, triacetin, tripropinoin, diacetin, dibutyl phthalate, acetyl monoglyceride, polyethylene glycols, castor oil, triethyl citrate, polyhydric alcohols, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, glyceryl monocaprylate, and glyceryl monocaprate. In one embodiment, the plasticizer is dibutyl sebacate. The amount of plasticizer used in the polymeric material typically ranges from about 10% to about 50%, for example, about 10%, 20%, 30%, 40%, or 50%, based on the weight of the dry polymer.

Anti-foaming agents can also be included. In one embodiment, the anti-foaming agent is simethicone. The amount of anti-foaming agent used typically comprises from about 0% to about 0.5% of the final formulation.

The amount of polymer to be used in the membrane-modified formulations is typically adjusted to achieve the desired drug delivery properties, including the amount of drug to be delivered, the rate and location of drug delivery, the time delay of drug release, and the size of the multiparticulates in the formulation. The amount of polymer applied typically provides an about 10% to about 100% weight gain to the cores. In one embodiment, the weight gain from the polymeric material ranges from about 25% to about 70%.

The combination of all solid components of the polymeric material, including co-polymers, fillers, plasticizers, and optional excipients and processing aids, typically provides an about 10% to about 450% weight gain on the cores. In one embodiment, the weight gain is about 30% to about 160%.

The polymeric material can be applied by any known method, for example, by spraying using a fluidized bed coater (e.g., Wurster coating) or pan coating system. Coated cores are typically dried or cured after application of the polymeric material. Curing means that the multiparticulates are held at a controlled temperature for a time sufficient to provide stable release rates. Curing can be performed, for example, in an oven or in a fluid bed drier. Curing can be carried out at any temperature above room temperature.

A sealant or barrier can also be applied to the polymeric coating. A sealant or barrier layer can also be applied to the core prior to applying the polymeric material. A sealant or barrier layer is not intended to modify the release of the at least one α3 β4 antagonist. Suitable sealants or barriers are permeable or soluble agents such as hydroxypropyl methylcellulose, hydroxypropyl cellulose, hydroxypropyl ethylcellulose, and xanthan gum.

Other agents can be added to improve the processability of the sealant or barrier layer. Such agents include talc, colloidal silica, polyvinyl alcohol, titanium dioxide, micronized silica, fumed silica, glycerol monostearate, magnesium trisilicate, and magnesium stearate, or a mixture thereof. The sealant or barrier layer can be applied from solution (e.g., aqueous) or suspension using any known means, such as a fluidized bed coater (e.g., Wurster coating) or pan coating system. Suitable sealants or barriers include, for example, OPADRY WHITE Y-1-7000 and OPADRY OY/B/28920 WHITE, each of which is available from Colorcon Limited, England.

The invention also provides an oral dosage form containing a multiparticulate α3 β4 antagonist formulation as hereinabove defined, in the form of caplets, capsules, particles for suspension prior to dosing, sachets, or tablets. When the dosage form is in the form of tablets, the tablets can be disintegrating tablets, fast dissolving tablets, effervescent tablets, fast melt tablets, and/or mini-tablets. The dosage form can be of any shape suitable for oral administration of a drug, such as spheroidal, cube-shaped, oval, or ellipsoidal. The dosage forms can be prepared from the multiparticulates in any known manner and can include additional pharmaceutically acceptable excipients.

All of the particular embodiments described above, including but not limited to, matrix-based, osmotic pump-based, soft gelatin capsules, and/or membrane-modified forms, which can further take the form of monolithic and/or multi-unit dosage forms, can have a functional coating. Such coatings generally serve the purpose of delaying the release of the drug for a predetermined period. For example, such coatings can allow the dosage form to pass through the stomach without being subjected to stomach acid or digestive juices. Thus, such coatings can dissolve or erode upon reaching a desired point in the gastrointestinal tract, such as the upper intestine.

Such functional coatings can exhibit pH-dependent or pH-independent solubility profiles. Those with pH-independent profiles generally erode or dissolve away after a predetermined period, and the period is generally directly proportional to the thickness of the coating. Those with pH-dependent profiles, on the other hand, can maintain their integrity while in the acid pH of the stomach, but quickly erode or dissolve upon entering the more basic upper intestine.

Thus, a matrix-based, osmotic pump-based, or membrane-modified formulation can be further coated with a functional coating that delays the release of the drug. For example, a membrane-modified formulation can be coated with an enteric coating that delays the exposure of the membrane-modified formulation until the upper intestine is reached. Upon leaving the acidic stomach and entering the more basic intestine, the enteric coating dissolves. The membrane-modified formulation then is exposed to gastrointestinal fluid, and releases at least one α3 β4 antagonist over an extended period, in accordance with the invention. Examples of functional coatings such as these are known in the art.

The thickness of the polymer in the formulations, the amounts and types of polymers, and the ratio of water-soluble polymers to water-insoluble polymers in the modified-release formulations are generally selected to achieve a desired release profile of the at least one α3 β4 antagonist. For example, by increasing the amount of water-insoluble-polymer relative to the water-soluble polymer, the release of the drug can be delayed or slowed.

Any formulation of the present invention can also contain a suitable compound that enhances the absorption of the at least one α3 β4 antagonist. These enhancers include, but are not limited to, cell envelope disordering compounds, solvents, steroidal detergents, bile salts, chelators, surfactants, non-surfactants, fatty acids, and mixtures thereof. The organic solvent can be selected from, but is not limited to, a $C_2$ or $C_3$ alcohol, a $C_3$ or $C_4$ diol, dimethylsulfoxide, N,N-dimethylformamide, 1-n-dodecyl-cyclazacyclo-heptan-2-one, N-methylpyrrolidone, N-(2-hydroxyethyl)pyrrolidone, triacetin, propylene carbonate and dimethyl isosorbide and mixtures thereof. The cell-envelope disordering compounds that can be used include, but are not limited to, isopropyl myristate, methyl laurate, oleic acid, oleyl alcohol, glycerol monooleate, glycerol dioleate, glycerol trioleate, glycerol monostearate, glycerol monolaurate, propylene glycol monolaurate, sodium dodecyl sulfate, and sorbitan esters and mixtures thereof. Bile salts that can be used include, but are not limited to, natural and synthetic salts of cholanic acid and mixtures thereof.

The amount of the dose administered, as well as the dose frequency, will vary depending on the particular dosage form used and route of administration. The amount and frequency of administration will also vary according to the age, body weight, and response of the individual subject. Typical dosing regimens can readily be determined by a competent physician without undue experimentation. It is also noted that the clinician or treating physician will know how and when to interrupt, adjust, or terminate therapy in conjunction with individual subject response.

In general, the total daily dosage for treating, modifying, and/or managing the abnormal increases in gastrointestinal motility and/or the intestinal conditions that cause the same, with any of the formulations according to the present invention, is from about 0.2 mg to about 40 mg, or from about 0.5 mg to about 20 mg, or from about 1 mg to about 15 mg, or from about 2 mg to about 12 mg, or any amount in between, of at least one α3 β4 antagonist such as N-2,3,3-tetramethyl-bicyclo-[2.2.1]heptan-2-amine, or a pharmaceutically acceptable salt thereof. For example, for an orally administered dosage form of, e.g., N-2,3,3-tetramethylbicyclo-[2.2.1]heptan-2-amine, or a pharmaceutically acceptable salt thereof, the total daily dose can range from about 0.5 mg to about 20 mg, or from about 1 mg to about 15 mg, or from 2 mg to about 12 mg. Accordingly, a single oral dose can be formulated to contain about 0.2 mg, 0.5 mg, 1 mg, 2 mg, 2.5 mg, 3 mg, 4 mg, 5 mg, 6 mg, 8 mg, 10 mg, 12 mg, 15 mg, 20 mg, or any amount in between, of N-2,3,3-tetramethylbicyclo-[2.2.1]heptan-2-amine, or a pharmaceutically acceptable salt thereof.

In the case of transdermal formulations, an excess of at least one α3 β4 antagonist can be incorporated into the transdermal system in order to ensure an effective concentration gradient for transdermal absorption. Thus transdermal units can contain from about 0.2 mg to about 120 mg, or from about 0.5 mg to about 100 mg, or from about 1 mg to about 80 mg, or from about 2 mg to about 60 mg, or any amount in between, of, e.g., N-2,3,3-tetramethylbicyclo-[2.2.1]heptan-2-amine.

The pharmaceutical formulations described herein can be formulated such that the maximum plasma concentration of the at least one α3 β4 antagonist can be achieved at about 3.5, 4, 5, 6, 7, 8, 9, 10, 12, 14, 18, or 24 hours, or anytime in between, following a first administration of the formulation of the present invention.

The pharmaceutical formulations containing at least one α3 β4 antagonist, or a pharmaceutically acceptable salt thereof, can be administered in single or in divided doses, 1, 2, 3, 4, 5, or more times each day. Alternatively, the dose can be delivered one or more times every 2, 3, 4, 5, 6, 7, or more days. In one embodiment, the pharmaceutical formulations are administered once per day.

Furthermore, the inventive methods suitable for oral, intranasal, buccal or sublingual administration provide an in vitro release profile in which, e.g., when measured by a U.S. Pharmacopoeia (USP) Type 1 Apparatus (baskets) or U.S. Pharmacopeia (USP) Type 2 Apparatus (paddles) at 37° C. and 50 rpm or higher in phosphate buffer at pH 6.8 or higher for the measuring period, can exhibit the following dissolution profile: 2 hours: less than or equal to about 60%; 4 hours: less than or equal to about 70%; 8 hours: greater than or equal to about 50%; 12 hours: greater than or equal to about 65%; and 24 hours: greater than or equal to about 80%. In other embodiments, the oral formulation can exhibit the following profile: 2 hours: less than or equal to about 50%; 4 hours: less than or equal to about 65%; 8 hours: greater than or equal to about 60%; 12 hours: greater than or equal to about 70%; and 24 hours: greater than or equal to about 80%. In still other embodiments, the oral formulation can exhibit the following profile: 2 hours: less than or equal to about 40%; 4 hours: about 20% to about 60%; 8 hours: greater than or equal to about 70%; 12 hours: greater than or equal to about 75%; and 24 hours: greater than or equal to about 80%.

For example, transdermal formulations according to the present invention, when tested using modified Franz diffusion cells of human epidermis (according to methods adapted from Franz, J. Invest. Dermatol. 64:194-195 (1975) and GB-A-2 098 865), in ammonium phosphate buffer at pH 4.0 or higher, while stirring the receiving compartment, at 300 RPM for example, and maintaining the temperature at 32° C. for the duration of the study, can exhibit the following dissolution profile: 2 hours: less than or equal to about 40%; 4 hours: about 10% to about 70%; 8 hours: about 20% to about 80%;

12 hours: greater than or equal to about 40%; and 24 hours: greater than or equal to about 70%. In other embodiments, the transdermal formulation can exhibit the following profile: 2 hours: less than or equal to about 30%; 4 hours: about 15% to about 60%; 8 hours: about 30% to about 70%; 12 hours: greater than or equal to about 50%; and 24 hours: greater than or equal to about 75%. In still other embodiments, the transdermal formulation can exhibit the following profile: 2 hours: less than or equal to about 25%; 4 hours: about 20% to about 50%; 8 hours: about 40% to about 70%; 12 hours: greater than or equal to about 55%; and 24 hours: greater than or equal to about 80%.

Any of the pharmaceutical formulations and dosage forms described herein can further comprise at least one pharmaceutically active compound other than at least one α3 β4 antagonist, or a pharmaceutically acceptable salt thereof. Such compounds can be included to treat, modify, and/or manage gastrointestinal secretion being reduced, prevented, and/or managed with at least one α3 β4 antagonist, or a pharmaceutically acceptable salt thereof, or a different one. Those of skill in the art are familiar with examples of the techniques for incorporating additional active ingredients into formulations comprising at least one α3 β4 antagonist, or a pharmaceutically acceptable salt thereof. Alternatively, such additional pharmaceutically active compounds can be provided in a separate formulation and co-administered to a subject with a formulation according to the present invention. Such separate formulations can be administered before, after, or simultaneously with the administration of formulations of the present invention containing at least one α3 β4 antagonist, or a pharmaceutically acceptable salt thereof.

The additional pharmaceutically active compounds that can be used include, but are not limited to, other ganglionic blockers and/or nicotinic-receptor antagonists (such as hexamethonium, trimethaphan, chloroisondamine, erysodine, β-dihydroerythrodine, amantidine, perpidine, succinylcholine, decamethonium, tubocurarine (including isomers thereof such as d-tubocurarine), atracurium, doxacurium, mivicurium, pancuronium, rocuronium, and vencuronium, for example), agents that alter gastrointestinal motility, antispasmodics, antimuscarinic agents, glycopyrrolate, atropine, hyscomine, scopolamine, opiates (such as loperamide, diphenoxylate, difenoxine, codeine, morphine, oxymorphone, oxycontin, dihydrocodeine, and fentanyl, for example), 5-HT receptor agonists, 5-HT antagonists (such as alosetron hydrochloride, for example), calcium channel blockers (such as verapamil, including its intestinal selective isomers, for example), beta blockers (including beta blockers having effects on gastrointestinal function through neurogenic activity), agents used to treat various gastrointestinal symptoms and diseases including those that alter fluid transport across the gut or into or out of gastrointestinal cells, diuretics (such as amiloride and furosemide, for example), anti-diarrheals (such as bismuth and sandostatin, for example), $H_2$-antihistamines, proton pump inhibitors, antacids, anti-inflammatory agents, sulfasalazine, steroids (such as mineralocorticoids, corticosteroids/glucocorticosteriods, estrogens, prednisone, prednisolone, cortisol, cortisone, fluticasone, dexamethasone, and betamethasone, for example), 5-aminosalicylic acid, anti-infective agents (such as metronidazole, ciprofloxacin, and azathioprine, for example), immunomodulators (such as 6-mercaptopurine, cyclosporine, and methotrexate, for example), fish oil, remicade, heparin, nicotine, octreotide, and combinations thereof.

Combinations can be administered such that the at least one α3 β4 antagonist, or a pharmaceutically acceptable salt thereof, and the at least one other pharmaceutically active compound are contained in the same dosage form. Alternatively, the combinations can be administered such that the at least one α3 β4 antagonist and the at least one additional pharmaceutically active compound are contained in separate dosage forms and are administered concomitantly or sequentially. Combinations of the above-listed pharmaceutically active compounds with the at least one α3 β4 antagonist can be in different stereoisomeric forms such as racemic, enriched, substantially pure or pharmaceutically acceptable salts thereof, are also specifically contemplated.

The invention is further illustrated by reference to the following examples. It will be apparent to those skilled in the art that many modifications, both to the materials and methods, can be practiced without departing from the purpose and scope of the invention.

EXAMPLES

Example 1

Production of Adhesive Diffusion Controlled Transdermal Formulations

The mecamylamine transdermal formulation is a transdermal patch that contains mecamylamine blended with an acrylic adhesive that is coated onto a printed backing to produce transdermal patches. The transdermal patches evaluated in this study have loadings of 5.2 mg, 10.4 mg, and 15.6 mg of mecamylamine, which enables the delivery of 2 mg, 4 mg, or 6 mg of mecamylamine in a 24-hour application period.

| Ingredient | FUNCTION | % in Final Product | % in Final Product | % in Final Product |
|---|---|---|---|---|
| N-2,3,3-tetramethylbicyclo-[2.2.1]heptan-2-amine | Active | 3.2 | 3.2 | 3.2 |
| Acrylic Adhesive 87-2516 | Adhesive | 27.9 | 27.9 | 27.9 |
| Acrylic Adhesive 87-2196 | Adhesive | 9.3 | 9.3 | 9.3 |
| Silicone Adhesive | Adhesive | 41.5 | 41.5 | 41.5 |
| Nitrogen NF | Pressure gas and oxygen purge | — | — | — |
| Polyester Backing | Impermeable Backing Layer | 18.2 | 18.2 | 18.2 |
| Polyester Release Liner | Disposable Release Liner | — | — | — |
| TOTAL | | 100 | 100 | 100 |

Manufacture of the Acrylic Adhesive Blend. The blend is produced by the addition of two different acrylic adhesives into a stainless steel mixing vessel. The adhesives are blended together. The wet blend is coated onto a polyester release liner. The wet adhesive film was dried by heated air. The dried adhesive film exited the oven and was brought into contact with the paper release liner passing through a laminator. The dried acrylic adhesive, between the polyester and paper release liners, was then wound onto the main rewind roll.

Manufacture of Mecamylamine Adhesive Blend. The blend was produced by mixing silicone adhesive and mecamylamine in a pressure vessel.

Manufacture of the Mecamylamine Adhesive Laminate. The mecamylamine adhesive bend was coated onto a printed backing using a knife-over-roll coating head. The wet adhesive film was dried by heated air. The dried adhesive film exited the oven and was brought into contact with the paper release liner passing through a laminator. The dried acrylic adhesive, between the polyester and paper release liners, was then wound onto the main rewind roll. Additional adhesive layers can be added to modify the release profile. Individual transdermal patches were cut from this system with the strength and administered dose reflecting the surface area of the cut patch.

Example 2

Clinical Study

To assess the clinical experience with transdermal mecamylamine, the mecamylamine was prepared according to the transdermal form of Example 1. When the transdermal patches were administered to smokers but otherwise healthy subjects and contrasted with placebo control groups, the following pattern of effects was demonstrated.

| Side Effect | Mecamylamine | Placebo |
| --- | --- | --- |
| Constipation | 42% | 12% |
| Headache | 36% | 36% |
| Application | 25% | 21% |
| Dizziness | 17% | 16% |
| Nausea | 15% | 12% |
| Asthenia | 14% | 9% |
| Insomnia | 14% | 14% |
| Rash | 13% | 11% |

From that list of treatment emergent effects, GI motility is evidence by the incidence of constipation in comparison to the other effects. For example, the emergence of constipation as a significant effect (42% of patients reported constipation as a side effect) to occur along with the observation that mecamylamine exhibits selectivity α3 β4 sub-type of nAChR (compared $IC_{50}$ values for α3 β4 with other nAChR sub-types) evidences that α3 β4 sub-type of nAChR plays a role in gastrointestinal conditions and the use of such a receptor to influence gut motility and/or diarrhea symptoms can be a treatment option for gastrointestinal conditions.

In a second clinical trial, the frequency of treatment emergent effects typically associated with "ganglion blocking" activity was assessed. The following treatment emergent effects were found:

| Side Effect | Mecamylamine | Placebo |
| --- | --- | --- |
| Gastrointestinal | 4.36% | 25.5% |
| Constipation | 28.9% | 3.4% |
| Dry Mouth | 3.4% | 2.7% |
| Cardiac Disorder | 1.3% | 1.3% |
| Eye | 0.7% | 2.0% |
| Dizziness | 4.0% | 3.4% |
| Urinary Retention | 0.7% | 0% |
| Nausea | 5.4% | 6.7% |

From that list, it is further demonstrated that with the exception of GI effects such as constipation, there were no other significant effects observed and in particular, none of the effects traditionally associated with a non-selective ganglion blocking activity.

Example 3

Clinical Study

In order to demonstrate the therapeutic benefit of a selective α3 β4 sub-type nAChR antagonist, mecamylamine was administered to patients with dominant chronic diarrhea symptoms (e.g., functional diarrhea). The clinical trial was a randomized, double-blind, placebo-controlled, parallel group, forced dose escalation study, which evaluated the efficacy of mecamylamine versus placebo over a 12-week period following an 8-14 day run-in period. Mecamylamine was dosed once daily at 2 mg/day for the first 4 weeks, followed by forced titration (providing the previous dose was well tolerated) to 4 mg/day for the next 4 weeks, and further dose-escalated (providing the previous dose was well tolerated) to 6 mg/day for the last 4 weeks of therapy.

Eight-two patients (both male and female) meeting ROME II criteria (modified) for Functional Diarrhea were randomized in the study. Using an intent-to-treat analysis and the entire 12 weeks of dose-escalation therapy, the mecamylamine treated patients failed to show any statistically significant difference from placebo in the primary and secondary endpoints with the exception of an improvement in stool consistency at week 4 (i.e., the 2 mg/day treatment period) based on positive responses on at least 50% of the available daily reports.

However, significant improvements in stool consistency with mecamylamine treatment compared to placebo were noted in a smaller modified per-protocol population (n=35) for the entire dose-escalation as well as for each dose treatment phase.

While the dominant feature of functional diarrhea is an altered motility, there was also a contribution of altered gut secretion and the therapeutic benefit of mecamylamine was shown in the improved stool consistency (i.e., less than 75% of stools are scored 6 or 7 (loose/mushy or watery stools) on the Bristol Stool Scale).

For example, the following table summarizes the number of patients showing "improvement" in stool consistency. Prior to treatment, patients were to be experiencing >50% of the time, a mushy/watery stool consistency in at least 75% of their daily stools. "Improvement" represents a patient experiencing <50% of the time, a mushy/watery stool consistency in at least 75% of daily stools. For example, in week 4 of the mecamylamine treatment group, eight patients out of eighteen, i.e., 44.4%, experienced "improvement" in their stool consistency.

| Period | Mecamylamine | Placebo | p-Value (one-sided) |
| --- | --- | --- | --- |
| Entire Study | 8/18 (44.4%) | 3/17 (17.6%) | 0.038* |
| Week 4 | 8/18 (44.4%) | 2/17 (11.8%) | 0.004** |
| Week 8 | 8/18 (44.4%) | 3/17 (17.6%) | 0.038* |
| Week 12 | 9/18 (50.0%) | 4/17 (23.5%) | 0.048* |

*represents 0.05;
**represents <0.01.

The overall incidence of adverse events (AE's) was similar for both mecamylamine and placebo treated patients. For example, there was no clinically significant changes in blood pressure, as illustrated in FIGS. 1 and 2, further demonstrating the dissociation of the selective effects on gut secretion from the traditional activity of mecamylamine such as blood pressure lowering activity.

From FIG. 1, there were no observed notable changes in mean sitting systolic or diastolic blood pressure in either treatment group over the course of the study, with mean sitting systolic values remaining between about 124 mmHg and 129 mmHg and mean diastolic values remaining between 78 mmHg and 81 mmHg in both groups at all study visits.

Figure 2:
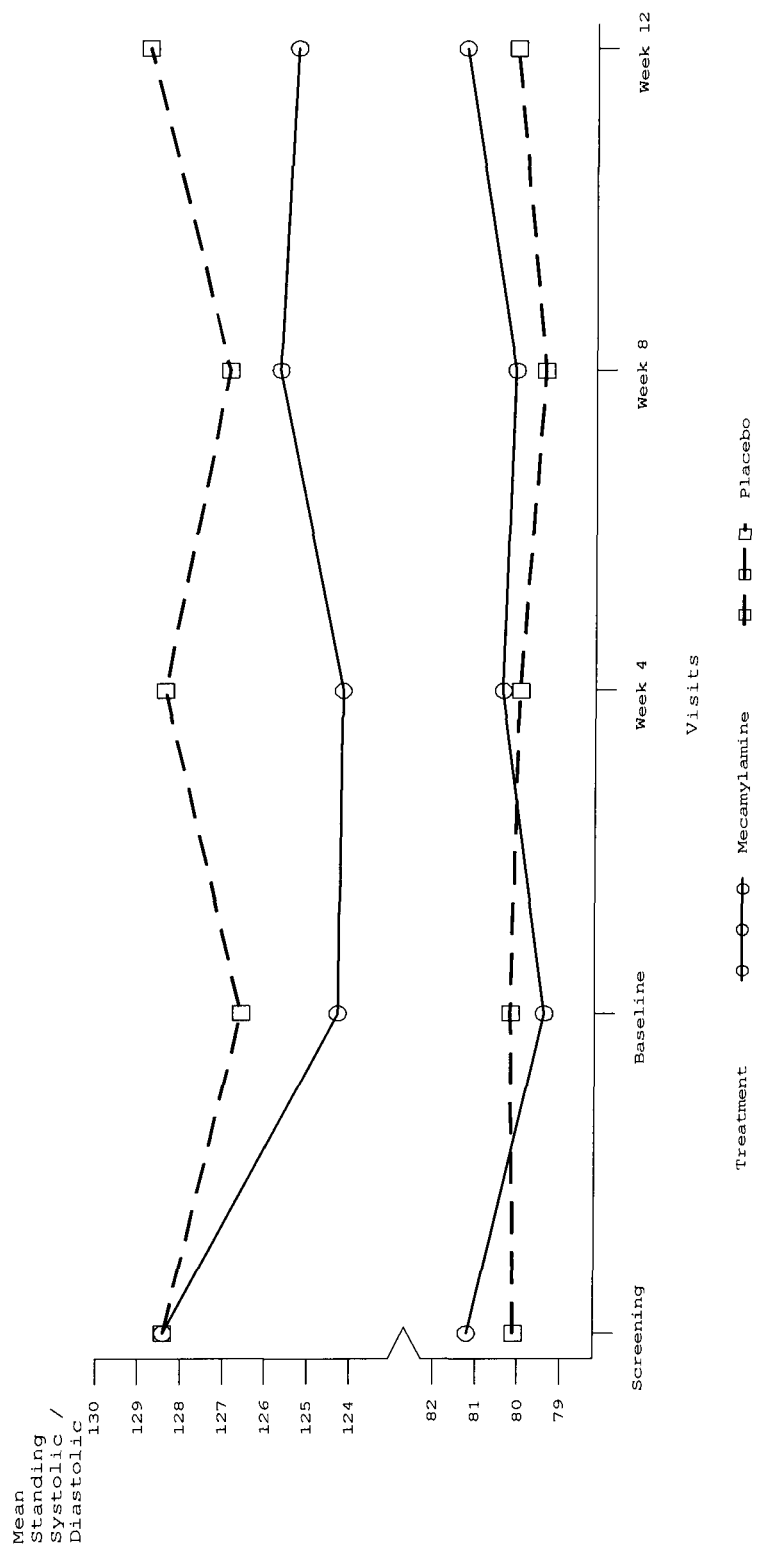
FIG. 2 is a graph of the mean standing systolic/diastolic blood pressure provided in Example 3.

From FIG. 2, there were no observed notable changes in mean standing systolic or diastolic blood pressure in either treatment group over the course of the study, with mean standing systolic values remaining between 124 mmHg and 130 mmHg and mean standing diastolic values remaining between 79 mmHg and 82 mmHg in both groups at all study visits.

What is claimed is:

1. A pharmaceutical composition comprising a therapeutically-effective amount of N-2,3,3-tetramethylbicyclo-[2.2.1] heptan-2-amine or pharmaceutically-acceptable salt thereof and at least one pharmaceutically-acceptable excipient in a modified-release formulation in a dosage form chosen from oral, intra-nasal, and transdermal forms; wherein:

N-2,3,3-tetramethylbicyclo-[2.2.1]heptan-2-amine exhibits an IC50 value for the α3 β4 sub-type of nAChR ranging from $1.0=10\text{-}6$ to $1\times10\text{-}9$ M or exhibits a potency for the α3 β4 nAChR sub-type at least two-times greater in comparison to at least one other nAChR sub-type;

the composition produces a peak:trough plasma level ratio of greater than zero to less than about 4:1;

the therapeutically-effective amount ranges from about 2 mg to about 12 mg per day;

the composition minimizes at least one side effect chosen from effects on heart rate, blood pressure, vision, and bladder function associated with a conventional formulation of the at least one an α3 β4 nAChR antagonist or pharmaceutically-acceptable salt thereof; and N-2,3,3-tetramethylbicyclo-[2.2.1]heptan-2-amine or the pharmaceutically-acceptable salt thereof is the sole active pharmaceutical compound in the composition.

2. The composition according to claim 1, wherein the N-2,3,3-tetramethylbicyclo-[2.2.1]heptan-2-amine comprises racemic N-2,3,3-tetramethylbicyclo-[2.2.1]heptan-2-amine, enriched (R)—N-2,3,3-tetramethylbicyclo-[2.2.1]heptan-2-amine, enriched (S)—N-2,3,3-tetramethylbicyclo-[2.2.1]heptan-2-amine, substantially pure (R)—N-2,3,3-tetramethylbicyclo-[2.2.1]heptan-2-amine, substantially pure (S)—N-2,3,3-tetramethylbicyclo-[2.2.1]heptan-2-amine, or pharmaceutically-acceptable salts of any of the foregoing.

3. The composition according to claim 2, wherein the N-2,3,3-tetramethylbicyclo-[2.2.1]heptan-2-amine comprises racemic N-2,3,3-tetramethylbicyclo-[2.2.1]heptan-2-amine, or a pharmaceutically-acceptable salt thereof.

4. The composition according to claim 2, wherein the N-2,3,3-tetramethylbicyclo-[2.2.1]heptan-2-amine comprises enriched (S)—N-2,3,3-tetramethylbicyclo-[2.2.1]heptan-2-amine, enriched (R)—N-2,3,3-tetramethylbicyclo-[2.2.1]heptan-2-amine, or pharmaceutically-acceptable salts thereof.

5. The composition according to claim 2, wherein the N-2,3,3-tetramethylbicyclo-[2.2.1]heptan-2-amine comprises substantially pure (S)—N-2,3,3-tetramethylbicyclo-[2.2.1]heptan-2-amine, substantially pure (R)—N-2,3,3-tetramethylbicyclo-[2.2.1]heptan-2-amine, or pharmaceutically acceptable salts thereof.

6. The composition according to claim 1, wherein the composition further comprises at least one immediate-release component.

7. The composition according to claim 1, wherein the composition comprises extended-release components, or delayed-release components, or both extended-release and delayed-release components.

8. The composition according to claim 1, wherein the composition is chosen from a matrix formulation, an osmotic pump-based formulation, and a modified-membrane formulation.

9. The composition according to claim 1, wherein the composition, when tested in a U.S. Pharmacopeia (USP) Type 2 Apparatus, at 37° C., stirred at 50 rpm, and in pH 6.8 phosphate buffer, releases less than about 60% of the at least one antagonist in less than about 2 hours;

greater than or equal to about 40% in about 12 or more hours; and about 70% or more in about 24 or more hours.

10. The composition according to claim 9, wherein the composition releases less than or equal to about 60% of the at least one antagonist in about 2 hours, less than or equal to about 70% in about 4 hours;

greater than or equal to about 50% in about 8 hours;

greater than or equal to about 65% in about 12 hours; and greater than or equal to about 80% in about 24 hours.

11. The composition according to claim 10, wherein the composition releases less than or equal to about 50% of the at least one antagonist in about 2 hours, less than or equal to about 65% in about 4 hours;

greater than or equal to about 60% in about 8 hours;

greater than or equal to about 70% in about 12 hours; and greater than or equal to about 80% in about 24 hours.

12. The composition according to claim 11, wherein the composition releases less than or equal to about 40% of the at least one antagonist in about 2 hours, from about 20% to about 60% in about 4 hours;

greater than or equal to about 70% in about 8 hours;

greater than or equal to about 75% in about 12 hours; and greater than or equal to about 80% in about 24 hours.

* * * * *

UNITED STATES PATENT AND TRADEMARK OFFICE
CERTIFICATE OF CORRECTION

PATENT NO.       : 9,040,591 B2                              Page 1 of 1
APPLICATION NO.  : 13/553453
DATED            : May 26, 2015
INVENTOR(S)      : John Devane It is certified that error appears in the above-identified patent and that said Letters Patent is hereby corrected as shown below:

Title page, item (54) and in the Specification, column 1, line 2 of the title,

"COMPRISING AT LEAST ONE α3 βA4 nAChR" should read --COMPRISING AT LEAST ONE α3 β4 nAChR--.

In the claims

Claim 1, col. 33, line 17,

"ranging from 1.0 =" should read --ranging from 1.0 ×--;

"10-6 to 1 × 10-9 M" should read --$10^{-6}$ to $1 \times 10^{-9}$ M--.

Claim 1, col. 33, line 28,

"the at least one an α3" should read --the at least one α3--.

Signed and Sealed this
Twentieth Day of October, 2015

Michelle K. Lee
*Director of the United States Patent and Trademark Office*